US009557319B2

(12) United States Patent
Keselowsky et al.

(10) Patent No.: US 9,557,319 B2
(45) Date of Patent: *Jan. 31, 2017

(54) CELL-BASED ARRAYS, METHODS OF MAKING, AND METHODS OF USING

(71) Applicant: University of Florida Research Foundation, Inc., Gainesville, FL (US)

(72) Inventors: Benjamin George Keselowsky, Gainesville, FL (US); Abhinav Prakash Acharya, Gainvesville, FL (US); Emina Huang, Gainesville, FL (US); Edward William Scott, Gainesville, FL (US); Matthew Carstens, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 193 days.

This patent is subject to a terminal disclaimer.

(21) Appl. No.: 14/285,024

(22) Filed: May 22, 2014

(65) Prior Publication Data

US 2014/0323353 A1    Oct. 30, 2014
US 2016/0349241 A9    Dec. 1, 2016

Related U.S. Application Data

(63) Continuation-in-part of application No. 13/373,051, filed on Nov. 2, 2011, now Pat. No. 9,012,202.

(60) Provisional application No. 61/826,139, filed on May 22, 2013, provisional application No. 61/409,223, filed on Nov. 2, 2010.

(51) Int. Cl.
| | |
|---|---|
| *C12M 1/00* | (2006.01) |
| *C12Q 1/00* | (2006.01) |
| *G01N 33/53* | (2006.01) |
| *G01N 33/567* | (2006.01) |
| *G01N 31/22* | (2006.01) |
| *C40B 30/06* | (2006.01) |
| *G01N 33/50* | (2006.01) |

(52) U.S. Cl.
CPC ....... *G01N 33/5011* (2013.01); *G01N 2500/10* (2013.01)

(58) Field of Classification Search
CPC ...... G01N 33/50; G01N 33/5011; C12M 1/00; C12Q 1/00; C40B 30/06
USPC ...... 435/4, 7.1, 7.21, 283.1, 287.2; 422/430; 506/10, 18
See application file for complete search history.

(56) References Cited

U.S. PATENT DOCUMENTS 6,406,745 B1    6/2002  Talton
2003/0032203 A1  2/2003  Sabatini et al.
2006/0141617 A1* 6/2006  Desai et al. .................. 435/325
2006/0251701 A1  11/2006 Lynn et al.
2009/0258057 A1  10/2009 Swiston et al.

FOREIGN PATENT DOCUMENTS

WO    WO2008086228    7/2008

OTHER PUBLICATIONS

Dalerba et al, Phenotypic characterization of human colorectal cancer stem cells, 2007, PNAS, 104, 10158-10163.*
Abhinav P. Acharya et al.; Adhesive substrate-modulation of adaptive immune responses; Biomaterials 29 (2008) 4736-4750 (15 pages).
Abhinav P. Acharya et al.; A high-throughput microparticle microarray platform for dendritic cell-targeting vaccines; Biomaterials 30 (2009) 4168-4177 (10 pages).
Scott G. Olenych et al.; Fibronectin and Cell Attachment to Cell and Protein Resistant Polyelectrolyte Surfaces; Biomacromolecules, 2005, 6, 3252-3258, (7 pages).
Emma M, E, Kristensen, et al.; Photoelectron Spectroscopy Studies of the Functionalization of a Silicon Surface with a Phosphorylcholine-Terminated Polymer Grafted onto (3-Aminopropyl)trimethoxysilane; Langmuir 2006, 22, 9651-9657, (7 pages).
C.M. Dekeyser et al.; A rough morphology of the adsorbed fibronectin layer favors adhesion of neuronal cells: Journal of Biomedical Materials Research Part A, pp.; Dec. 2007; 116-128, (13 pages).
M.L. Carot et al.; Structure of Mixed Carboxylic Acid Terminated Self-Assembled Monolayers: Experimental and Theoretical Investigation, J. Phys. Chem. C 2007, 111, 4294-4304 (11 pages).
S. Rammelt et al.; Coating of titanium implants with collagen, RGD peptide and chondroitin sulfate, Biomaterials, 27, 2006, 5561-5571 (11 pages).
Nathan E. Reticker-Flynn et al.; A combinatorial extracellular matrix platform identifies cellextracellular matrix interactions that correlate with metastasis; NIH Public Access, Author Manuscript , Nat Commun 2012, pp. 1-22 (22 pages).
N.F. Huang et al.; A Matrix Micropatterning Platform for Cell Localization and Stem Cell Fate Determination; NIH Public Access Author Manuscript; Acta Biomater. Author manuscript; Dec. 2010; 6(12): 4614-4621 (14 pages).
Emina H. Huang et al.; Aldehyde Dehydrogenase 1 Is a Marker for Normal and Malignant Human Colonic Stem Cells (SC) and Tracks SC Overpopulation during Colon Tumorigenesis; Cancer Res 2009; 69: 3382-3389; Apr. 15, 2009 (9 Pages).
Joseph E. Carpentino et al.; Aldehyde Dehydrogenase-Expressing Colon Stem Cells Contribute to Tumorigenesis in the Transition from Colitis to Cancer; Cancer Res 2009; 69: (20). Oct. 15, 2009, (9 pages).
Anitha Shenoy et al.; ALDH as a Marker for Enriching Tumorigenic Human Colonic Stem Cells; NIH Public Access Author Manuscript; Published in final edited form as: Methods Mol Biol. 2012 ; 916: 373-385, (12 pages).
Christopher J. Flaim et al.; An extracellular matrix microarray for probing cellular differentiation; Nature Publishing Group; Nature Methods, vol. 2, No. 2; Feb. 2005, pp. 119-125 (7 pages).
Masafumi Nakajima, et al.; Combinatorial protein display for the cell-based screening of biomaterials that direct neural stem cell differentiation; ScienceDirect, Biomaterials 28, 2007, pp. 1048-1060 (13 pages).

(Continued)

*Primary Examiner* — Narayan Bhat
(74) *Attorney, Agent, or Firm* — Thomas Horstemeyer, LLP

(57) ABSTRACT

Embodiments of the present disclosure provide for arrays, systems, and methods analyzing cells, methods of making arrays, and the like.

19 Claims, 35 Drawing Sheets

(56) References Cited

OTHER PUBLICATIONS

Christopher J. Flaim et al.; Combinatorial Signaling Microenvironments for Studying Stem Cell Fate; Stem Cells and Development 17:29-39; 2008, pp. 29-39 (11 pages).
Langer et al.; Controlled Release and Magnetically Modulated Systems for Macromolecular Drugs; Annals of the New York Academy of Sciences; Dec. 2006, pp. 1-13 (13 pages).
Ratmir Derda et al.; Defined Substrates for Human Embryonic Stem Cell Growth Identified from Surface Arrays; ACS Publications; ACS Chemical Biology; vol. 2, No. 5, pp. 347-355, 2007, (9 pages).
Yoav Soen; Detection and Characterization of Cellular Immune Responses Using Peptide-MHC Microarrays; PLOS Biology, vol. 1, Issue 3, pp. 429-438, Dec. 2003 (10 pages).
Gokhan Deviren et al.; Detection of antigen-specific T cells on p/MHC microarrays; Journal of Molecular Recognition, J. Mol. Recognit. 2007; 20: pp. 32-38 Published online Nov. 2006 in Wiley InterScience (7 pages).
Cheong Hoon Kwon et al.; Drug-Eluting Microarrays for Cell-Based Screening of Chemical-Induced Apoptosis; ACS Publication, Analytical Chemistry, Anal. Chem., 2011, 83 4118-4125; Publication Date (Web): Apr. 8, 2011 (8 pages).
Yoav Soen et al.; Exploring the regulation of human neural precursor cell differentiation using arrays of signaling microenvironmnets, Molecular Systems Biology (2006), Article No. 37; Mar. 2006, pp. 1-14 (14 pages).
Randolph S. Ashton et al.; High-Throughput Screening of Gene Function in Stem Cells Using Clonal Microarrays; Stem Cells 2007, vol. 25, Issue 11, pp. 2928-2935, (8 pages).
Bruce M. Boman et al.; Human Colon Cancer Stem Cells: A New Paradigm in Gastrointestinal Oncology; Journal of Clinical Oncology, Review Article, Jun. 10, 2008, vol. 26, No. 17, pp. 2828-2838 (11 pages).
Mark A. LaBarge et al.; Human mammary progenitor cell fate decisions are products of interactions with combinatorial microenvironments; www.rsc.org/ibiology, Integrative Biology, Issue 1, 2009, Interdisciplinary approaches for molecular and cellular life sciences, Published Nov. 2008, pp. 70-79 (10 pages).
Larissa Belov et al.; Immunophenotyping of Leukemias Using a Cluster of Differentiation Antibody Microarray; Cancer Research 61, Jun. 2001, pp. 4483-4489 (8 pages).
Daniel S. Chen et al.; Marked Differences in Human Melanoma Antigen-Specific T Cell Responsiveness after Vaccination Using a Functional Microarray; PLOS medicine, Oct. 2005, vol. 2, Issue 10, pp. 1018-1030 (13 pages).
Junaid Ziauddin et al.; Microarrays of cells expressing defined cDNAs; Nature, vol. 411, May 3, 2001, www.nature.com, pp. 107-110 (3 pages).
Steve N Bailey et al.; Microarrays of lentiviruses for gene function screens in immortalized and primary cells; Nature Methods, vol. 3, No. 2, Feb. 2006, pp. 117-122 (6 pages).
Steve N. Bailey; Microarrays of small molecules embedded in biodegradable polymers for use in mammalian cell-based screens; PNAS, vol. 101, No. 46, Nov. 16, 2004, pp. 16144-16149 (6 pages).
Julie A. Phillippi; Microenvironments Engineered by Inkjet Bioprinting Spatially Direct Adult Stem Cells Toward Muscle-and Bone-Like Subpopulations; StemCells 2008;26:127-134 www.StemCells.co, pp. 127-134 (8 pages).
Christopher S. Chen et al.; Micropatterned Surfaces for Control of Cell Shape, Position, and Function; Biotechnol. Prog. Dec. 1998, vol. 14, 356-363 (8 pages).
Salman R Khetani et al.; Microscale culture of human liver cells for drug development; Nature Biotechnology, vol. 26, No. 1, Jan. 2008, pp. 120-126 (7 pages).
Gabriel A. Kwong et al.: Modular Nucleic Acid Assembled p/MHC Microarrays for Multiplexed Sorting of Antigen-Specific T Cells; J. Am. Chem. Soc. Jun. 2009, 131, pp. 9695-9703 (9 pages).
Hidenori Otsuka; Nanofabrication of Nonfouling Surfaces for Micropatterning of Cell and Microtissue; Molecules, Aug. 2010, 15, pp. 5525-5546 (22 pages).
Daniel G Anderson et al.; Nanoliter-scale synthesis of arrayed biomaterials and application to human embryonic stem cells; Nature Biotechnology, vol. 22, No. 7, Jul. 2004, pp. 863-866 (4 pages).
C. Yue et al.; Novel Cellular Microarray Assay for Profiling T-Cell Peptide Antigen Specificities, Journal of Proteome Research, Sep. 2010, 9, 5629-5637 (9 pages).
Tiago G. Fernandes et al.; On-Chip, Cell-Based Microarray Immunofluorescence Assay for High-Throughput Analysis of Target Proteins; Analytical Chemistry, vol. 80, No. 17, Sep. 2008, pp. 6633-6639 (7 pages).
Xin Ting Zheng et al.; On-chip investigation of cell—drug interactions; Advanced Drug Delivery Reviews 65, Feb. 2013, pp. 1556-1574 (19 pages).
In Kap Ko et al.; Parallel analysis of multiple surface markers expressed on rat neural stem cells using antibody microarrays; Biomaterials 26, Jan. 2005, pp. 4882-4891 (10 pages).
James R. Falsey; Peptide and Small Molecule Microarray for High Throughput Cell Adhesion and Functional Assays; Bioconjugate Chem. Feb. 2001, 12, 346-353 (8 pages).
Dora Peelen; Specific Capture of Mammalian Cells by Cell Surface Receptor Binding to Ligand Immobilized on Gold Thin Films; Journal of Proteome Research 2006, 5, 1580-1585, May 2006, (8 pages).
Moo-Yeal Lee; Three-dimensional cellular microarray for high-throughput toxicology assays; PNAS, Jan. 2008, vol. 105, No. 1, 59-63, (5 pages).
Anitha K. Shenoy; Transition from Colitis to Cancer: High Wnt Activity Sustains the Tumor-Initiating Potential of Colon Cancer Stem Cell Precursors; Cancer Res 2012;72:5091-5100, Aug. 17, 2012, (11 pages).
Nazgul Tuleuova; Using growth factor arrays and micropatterned co-cultures to induce hepatic differentiation of embryonic stem cells; Biomaterials 31, Sep. 2010, 9221-9231, (11 pages).

* cited by examiner

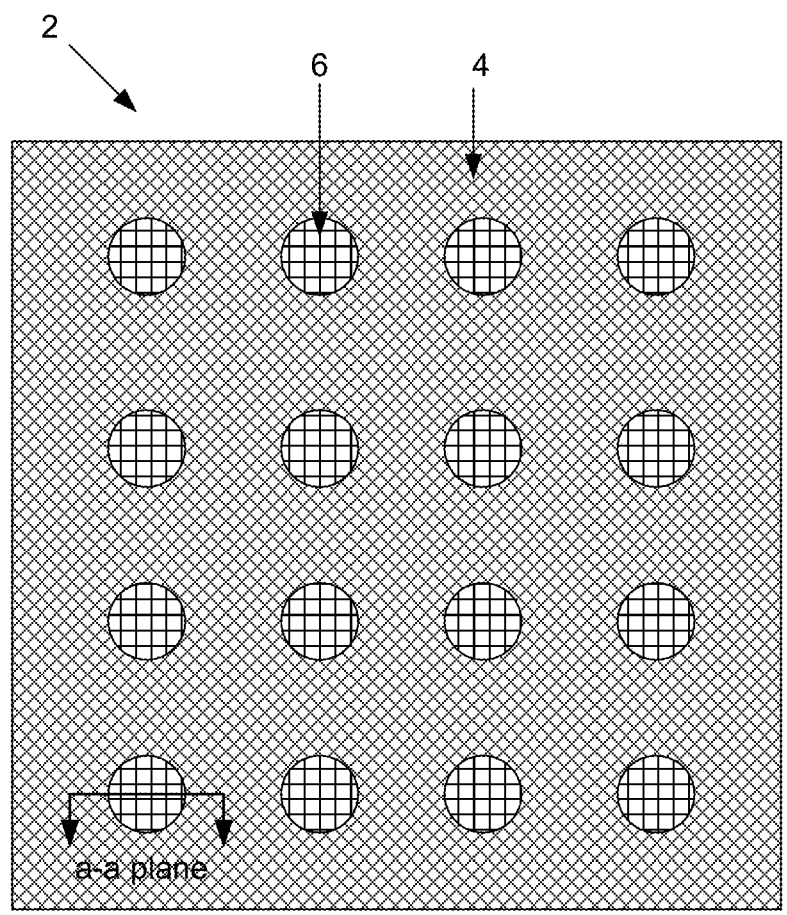
FIG. 1.1
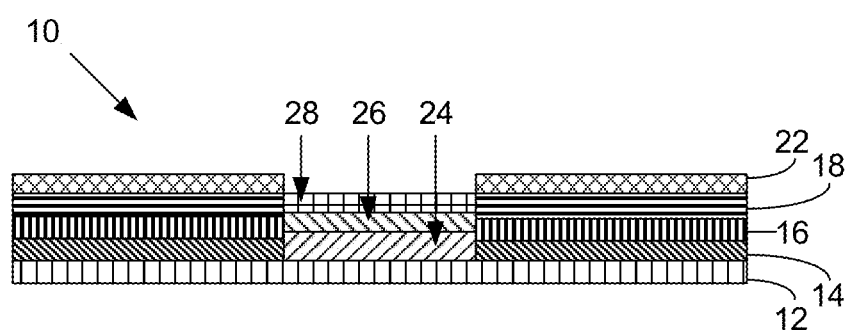
FIG. 1.2
a-a plane

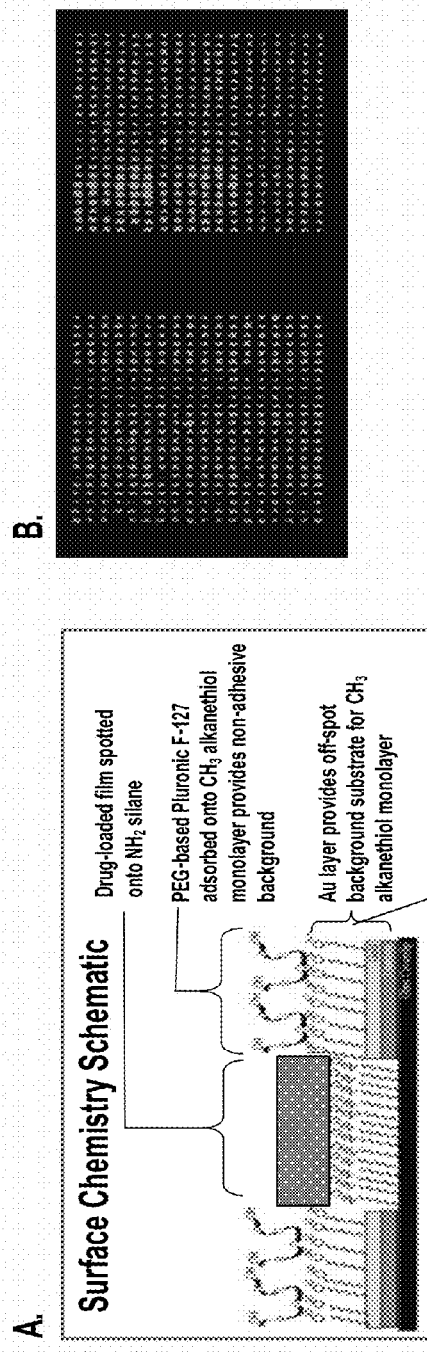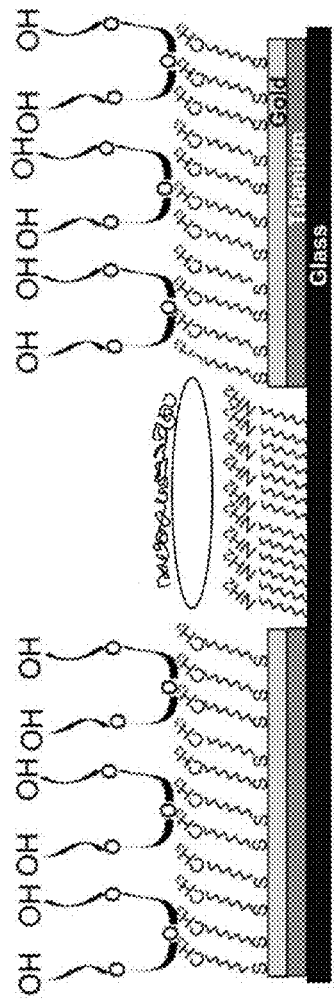
FIG. 1.3
Array Fabrication Schematic. A. Surface chemistry schematic is shown of a single arrayed spot. B. Representative microarray illustrating more than 1,000 spots arrayed onto a standard glass slide.

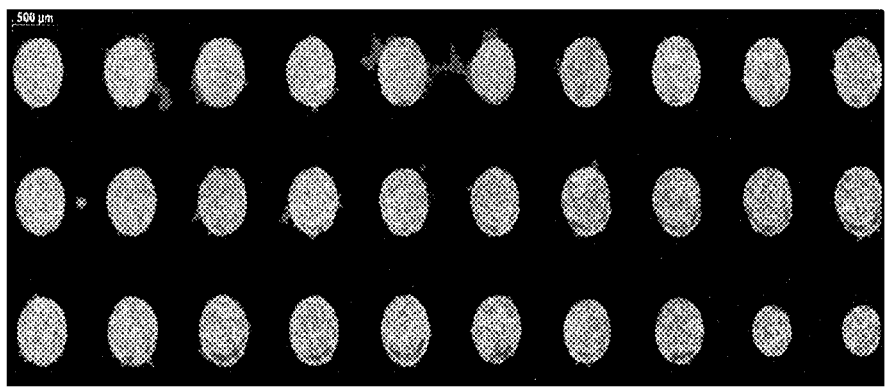
FIG. 2.1
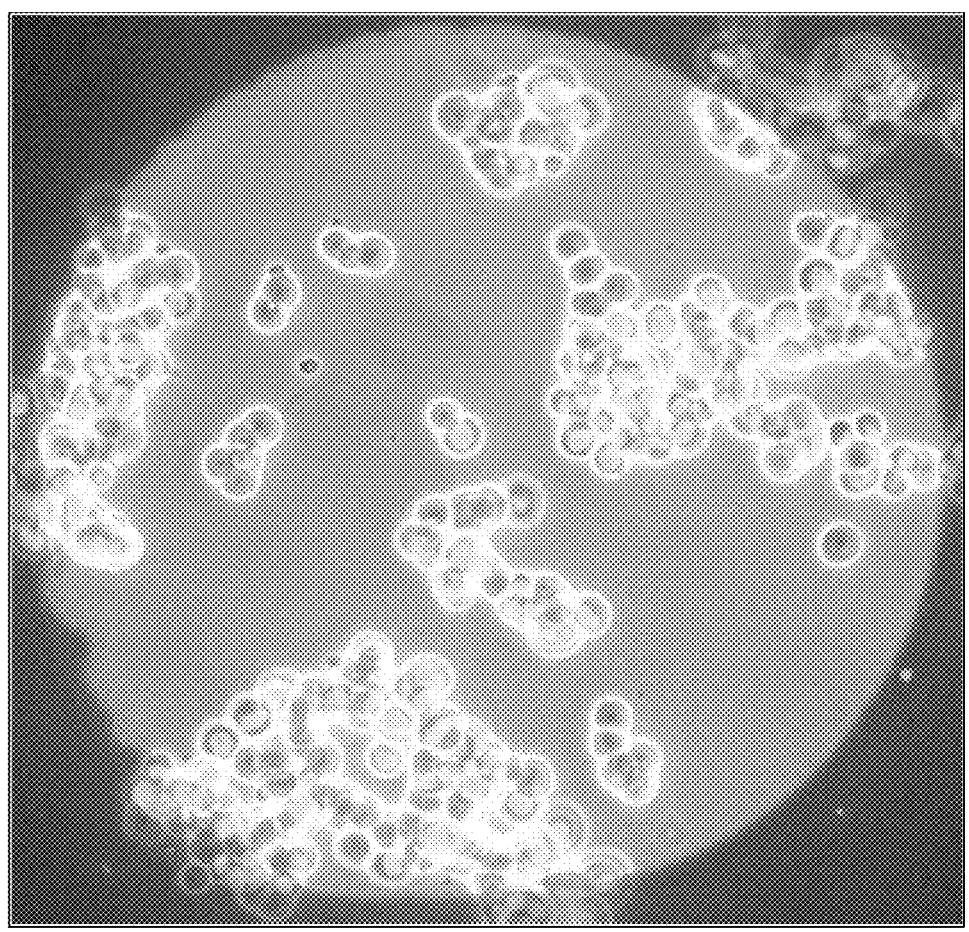
FIG. 2.2A

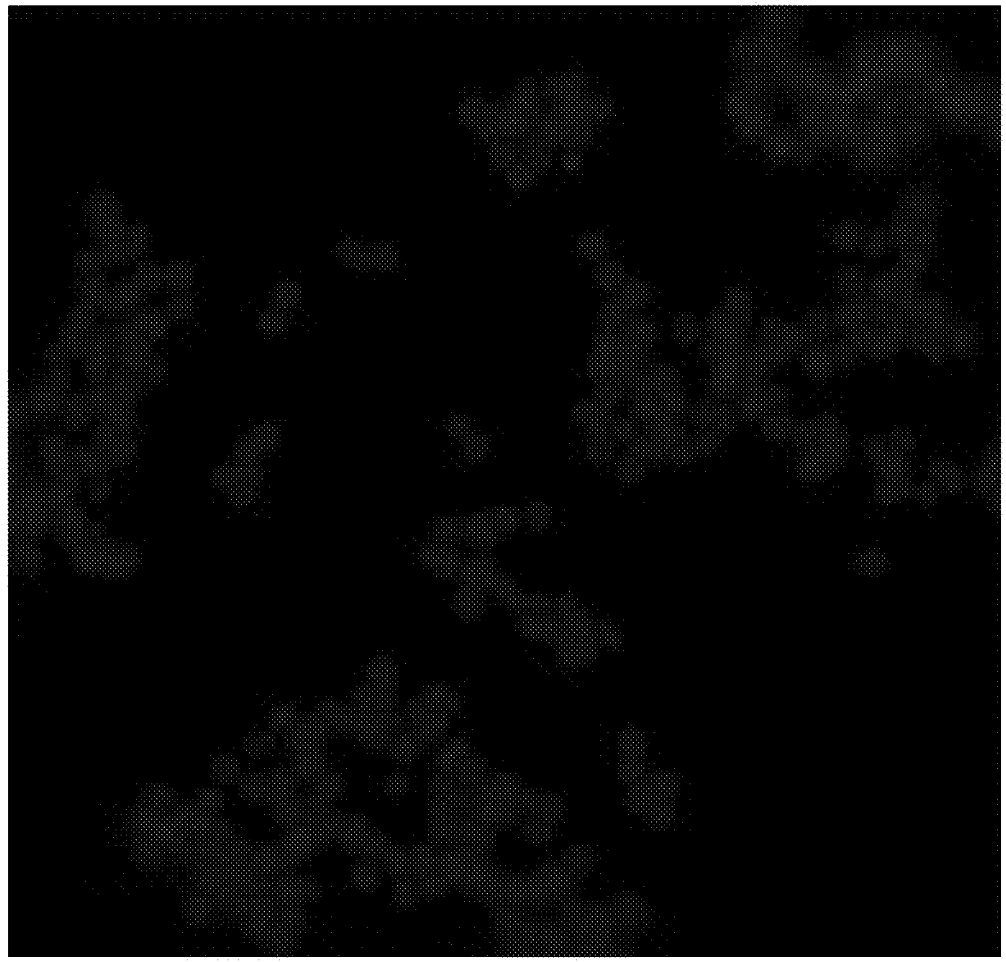
FIG. 2.2B

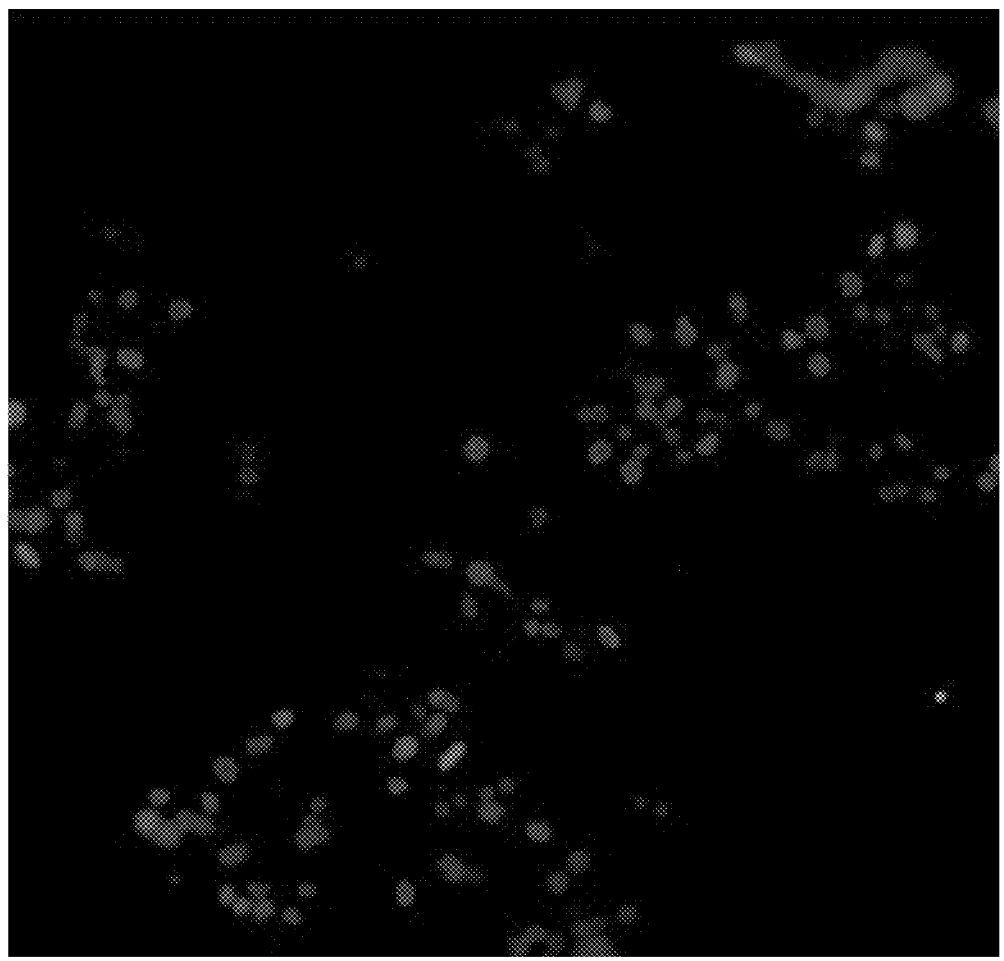
FIG. 2.2C

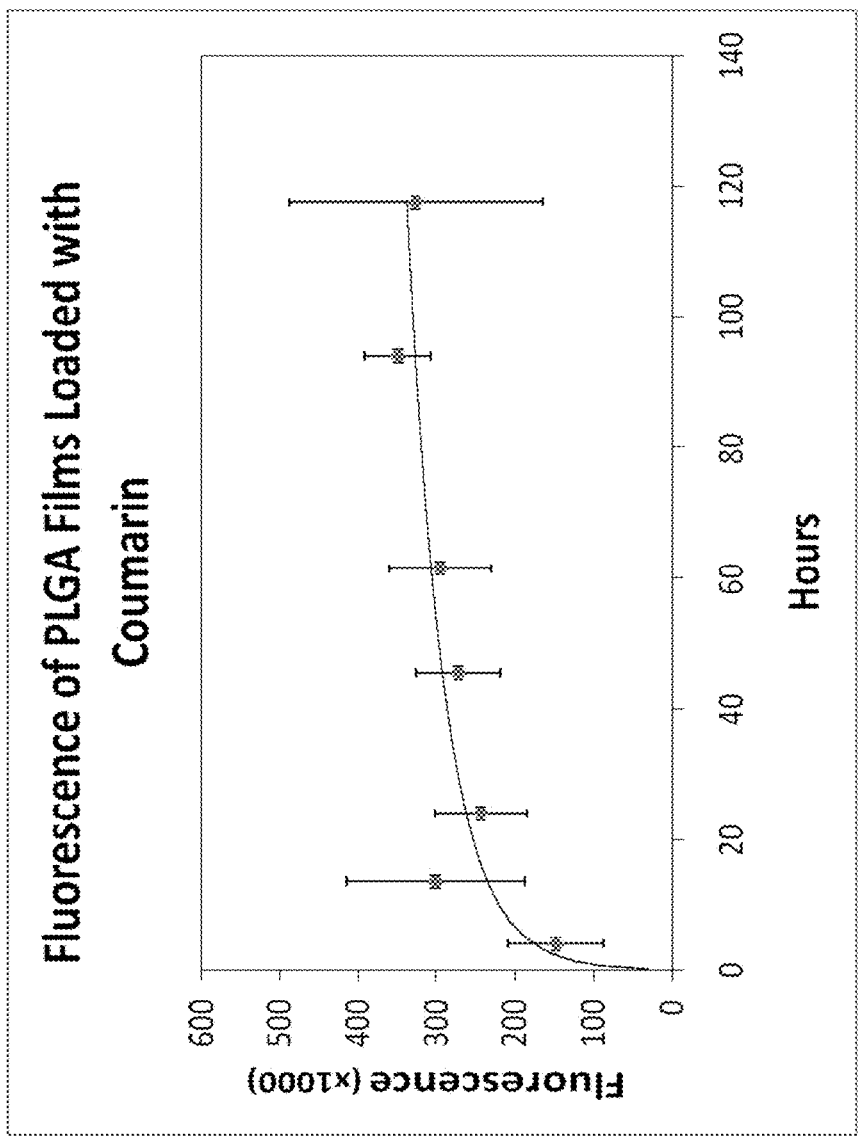
FIG. 2.3

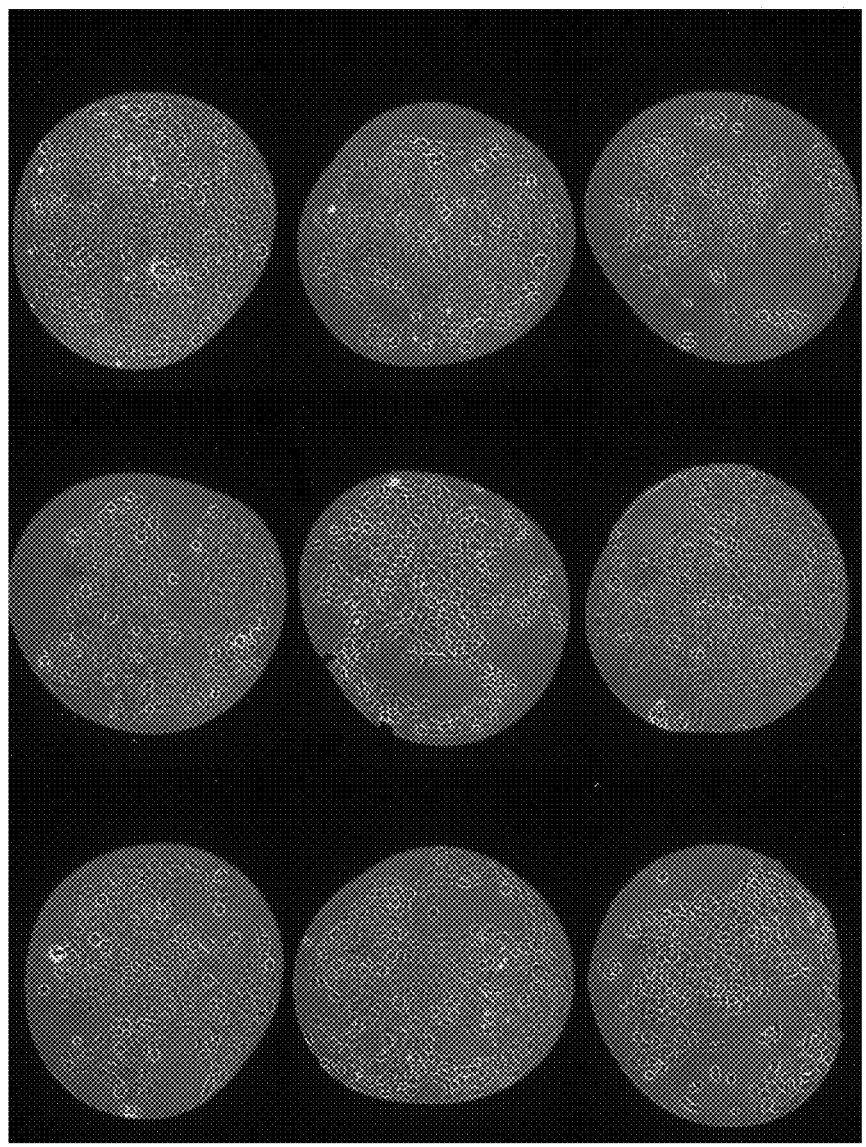
FIG. 3.1

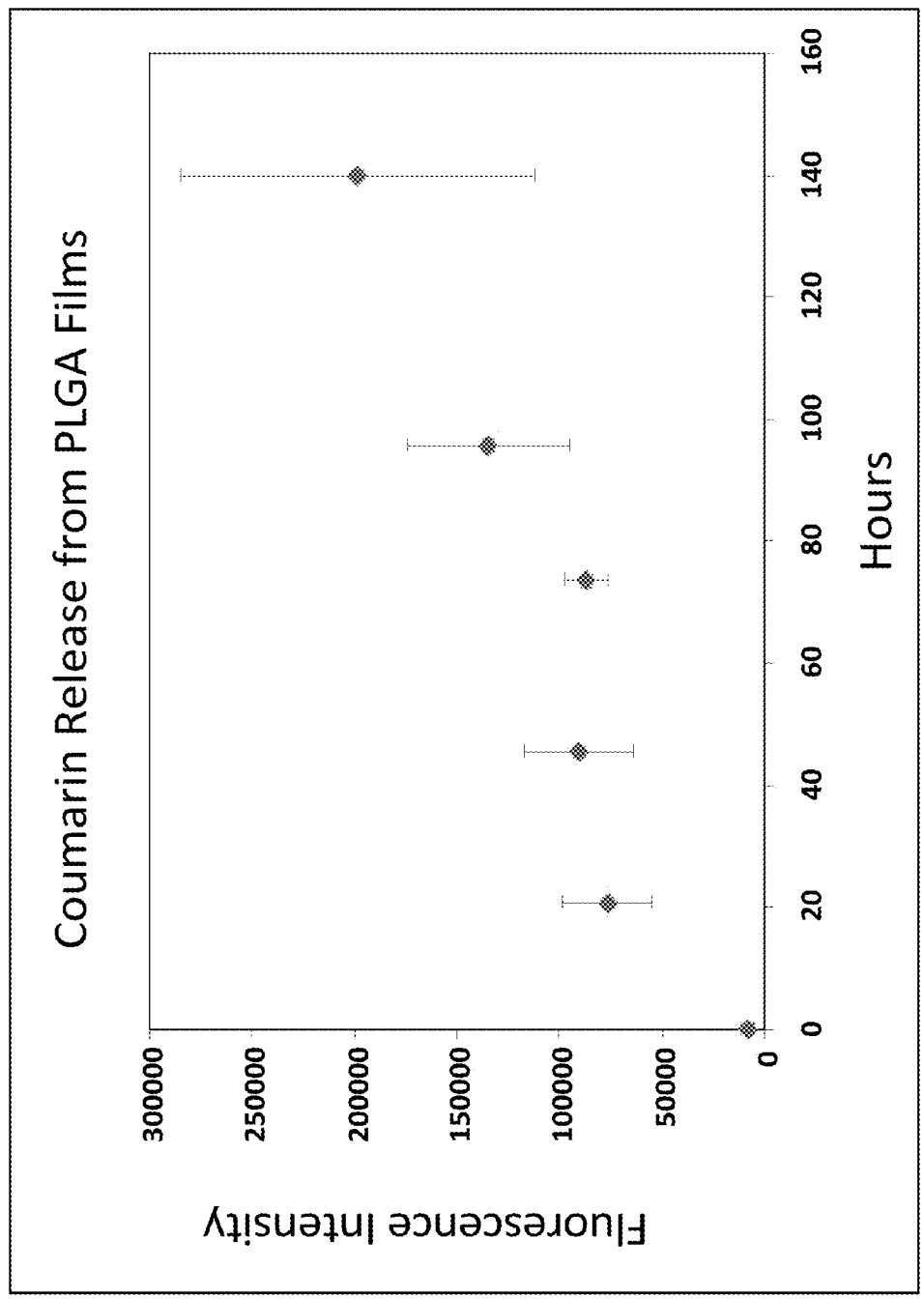
FIG. 3.2

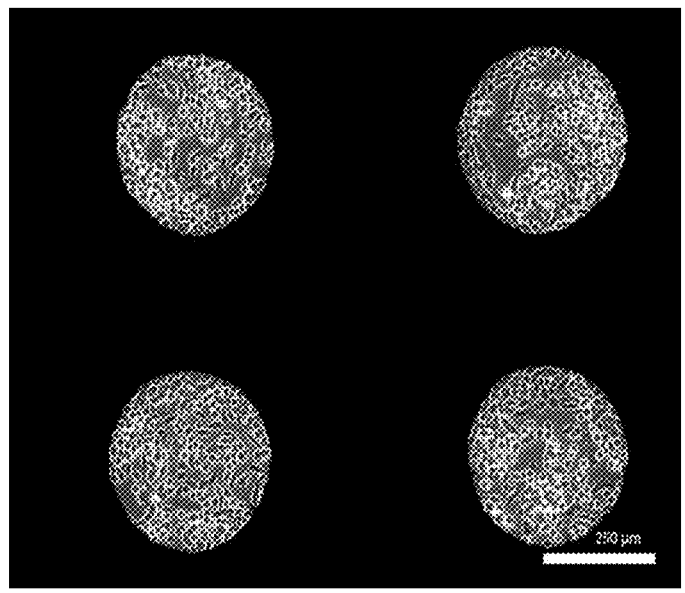
FIG. 4.1
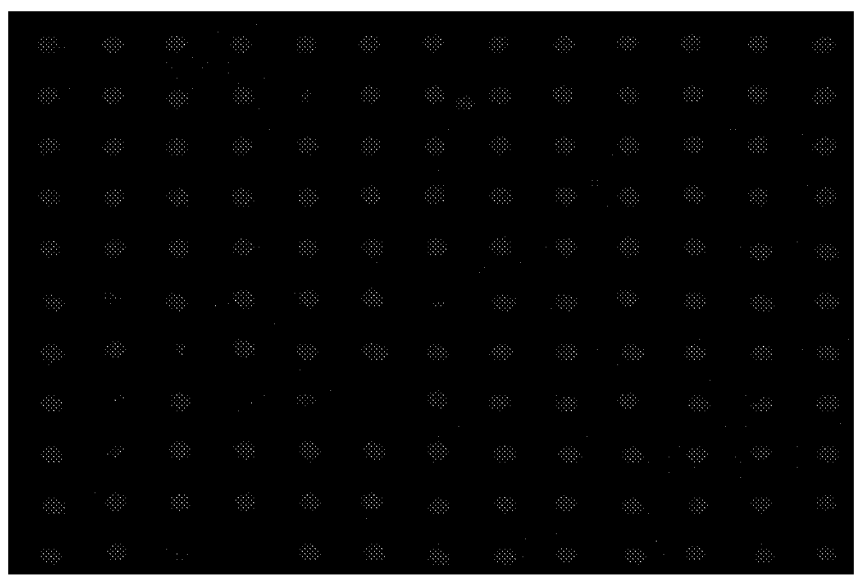
FIG. 4.2

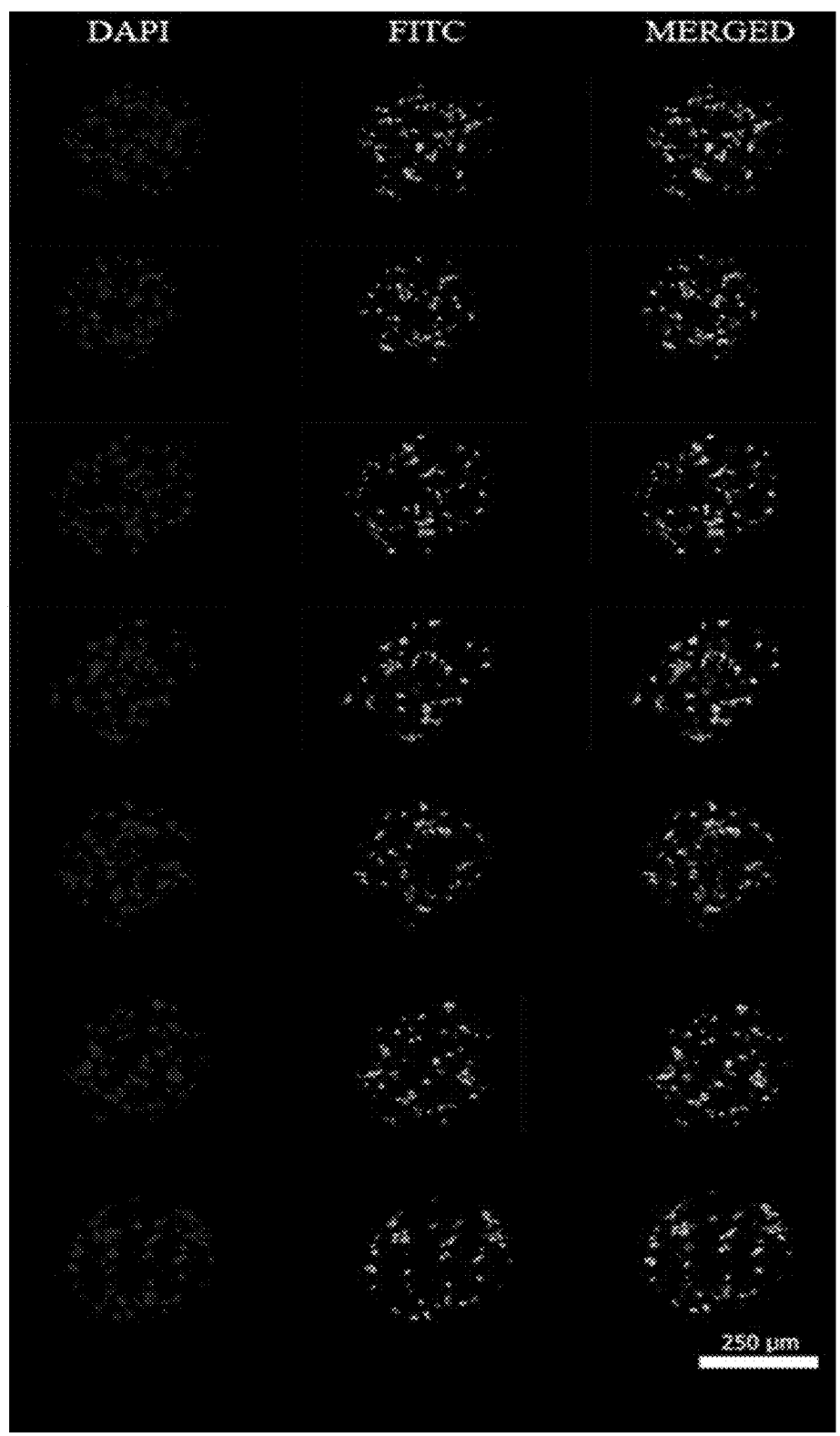
FIG. 4.3

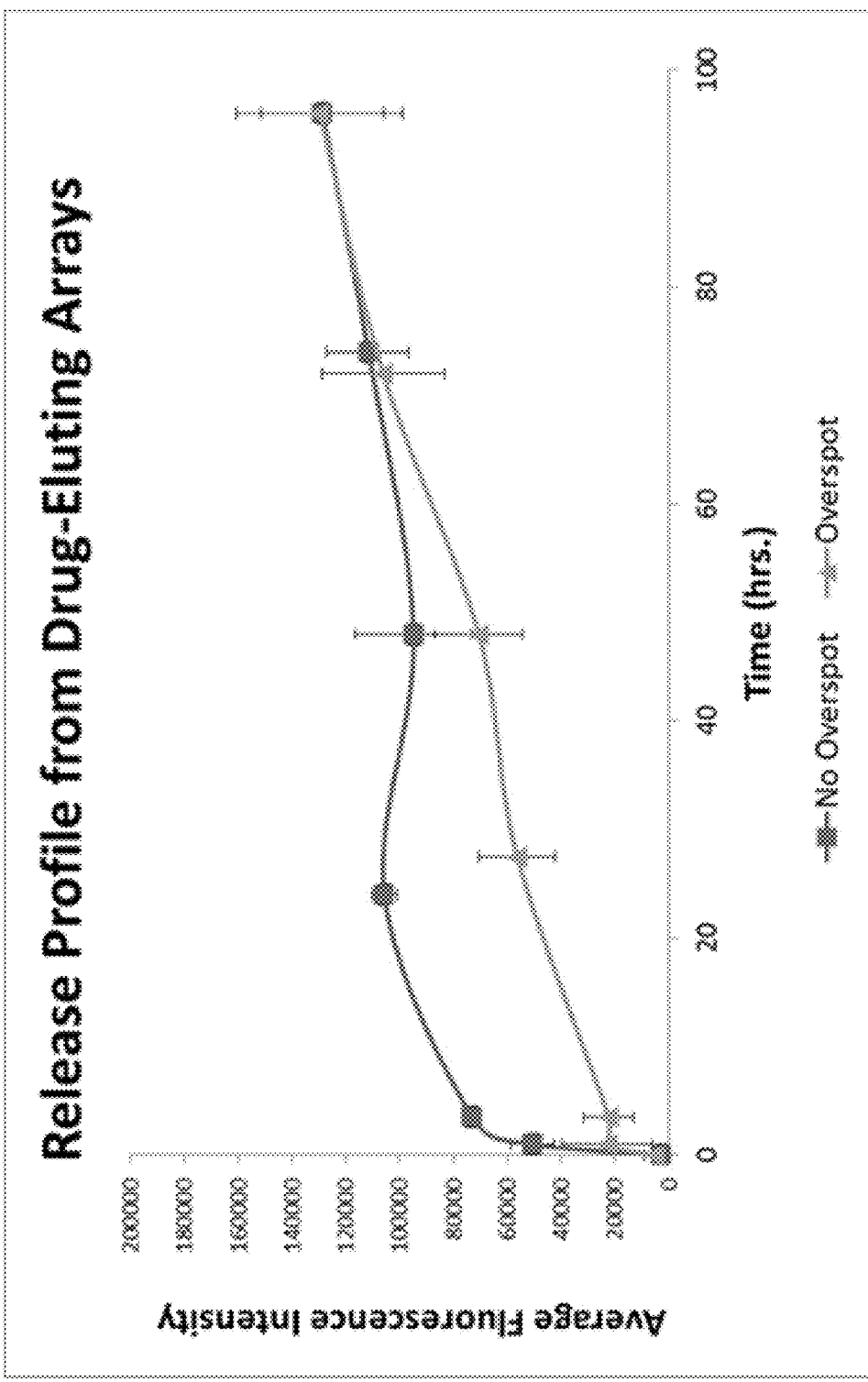
FIG. 4.4

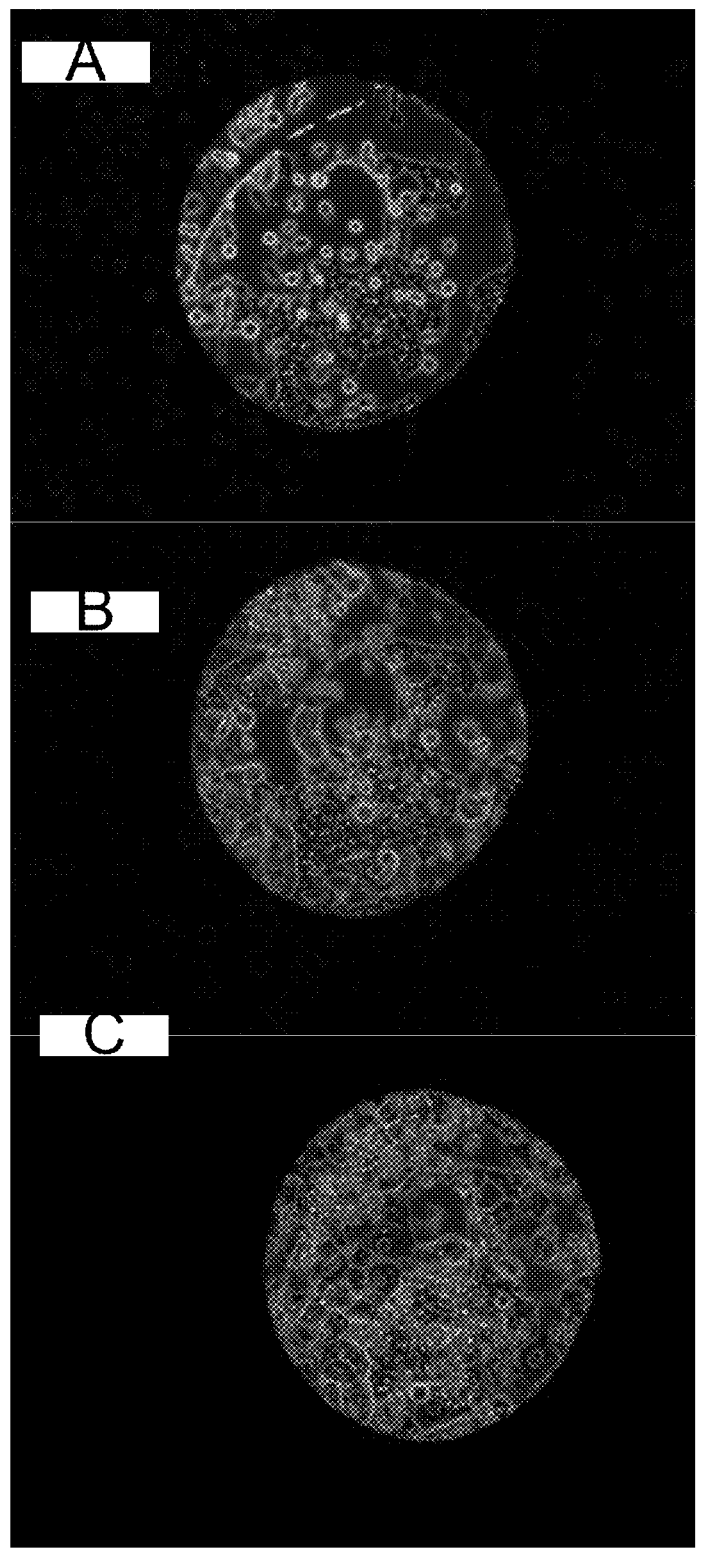
FIG. 5.1A-5.1C

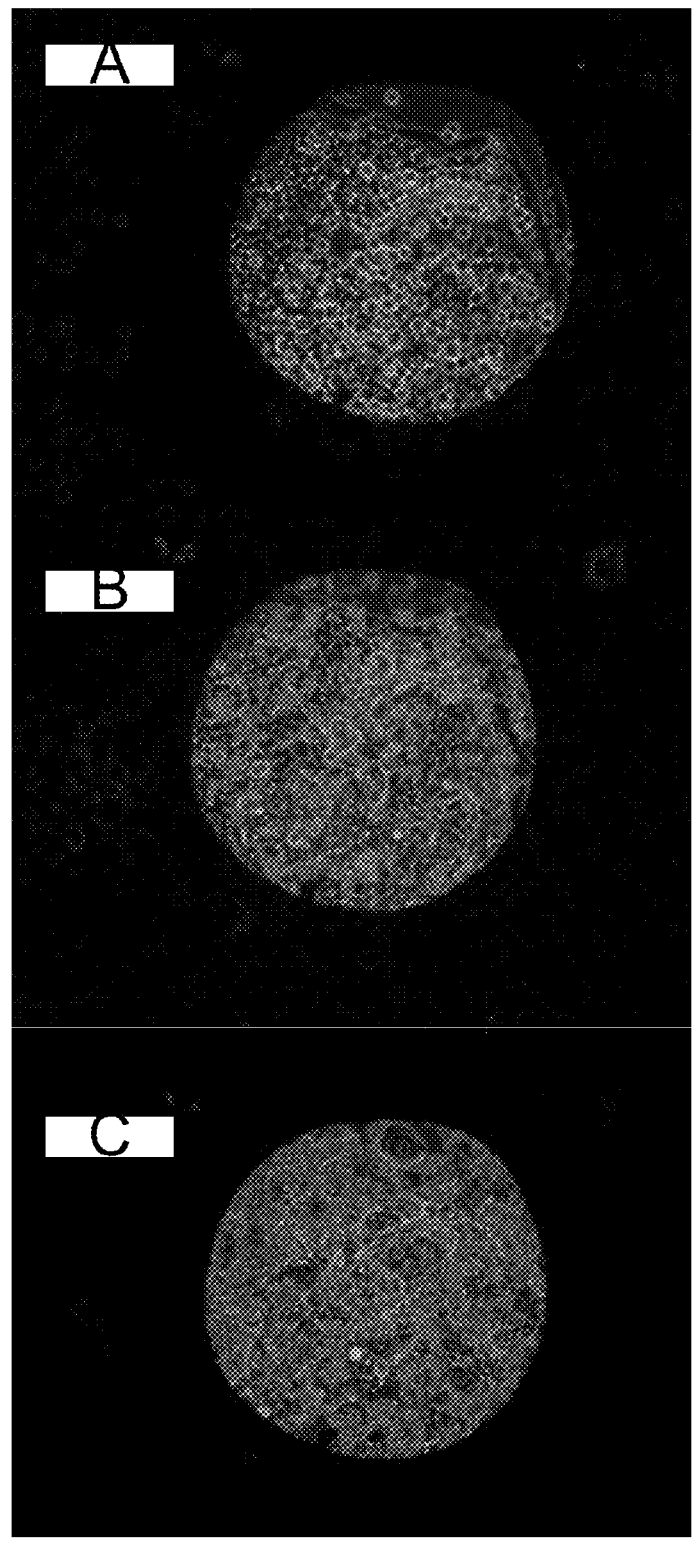
FIG. 5.2A-5.2C

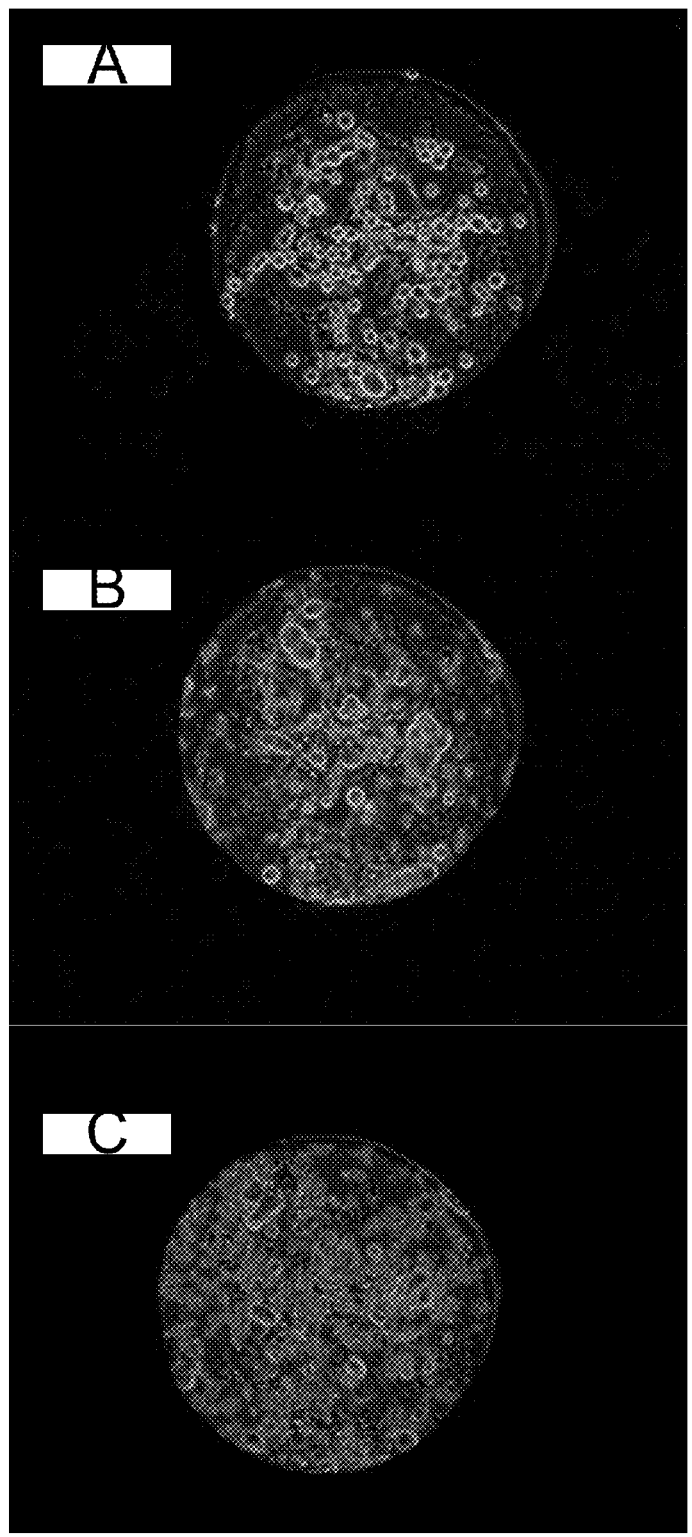
FIG. 5.3A-5.3C

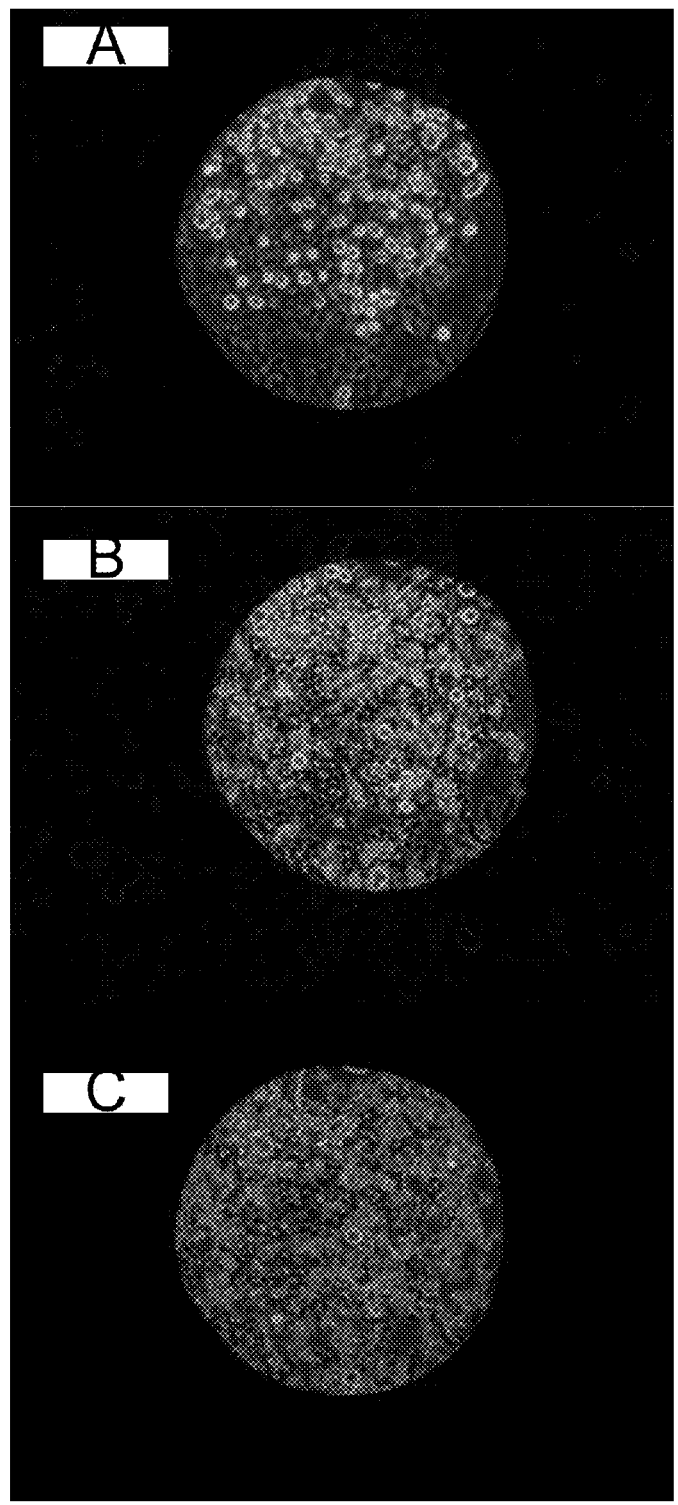
FIG. 5.4A-5.4C

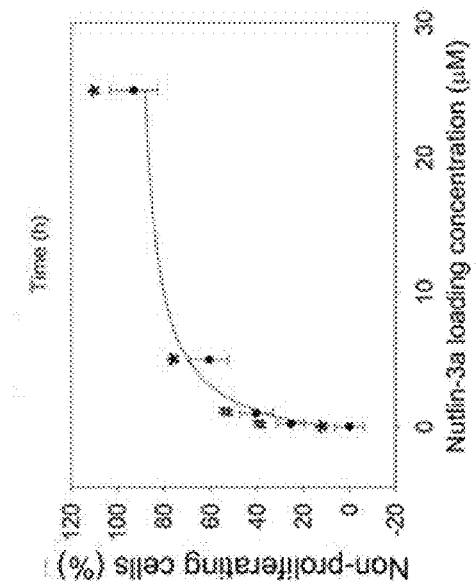
FIG. 7A
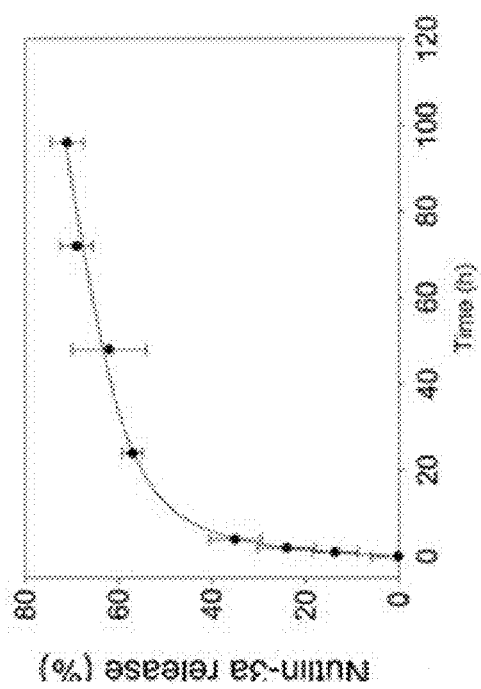
FIG. 7B
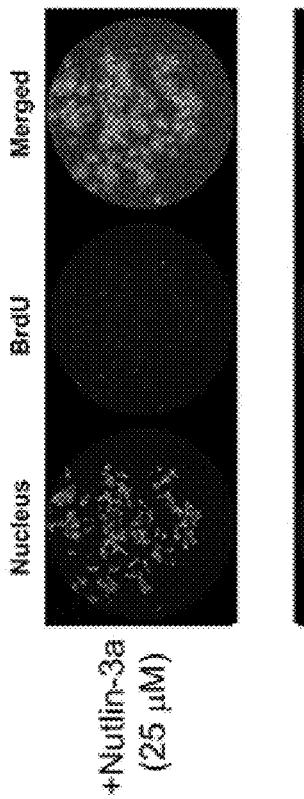
FIG. 7C
FIG. 7D
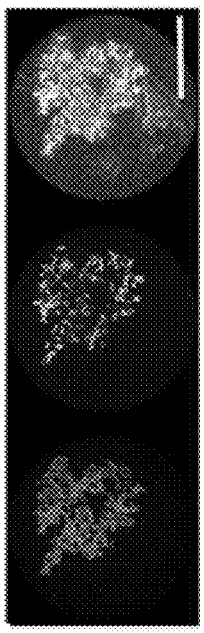

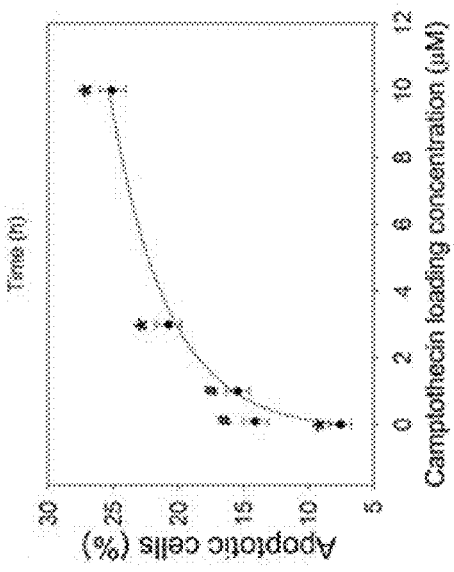
FIG. 7E
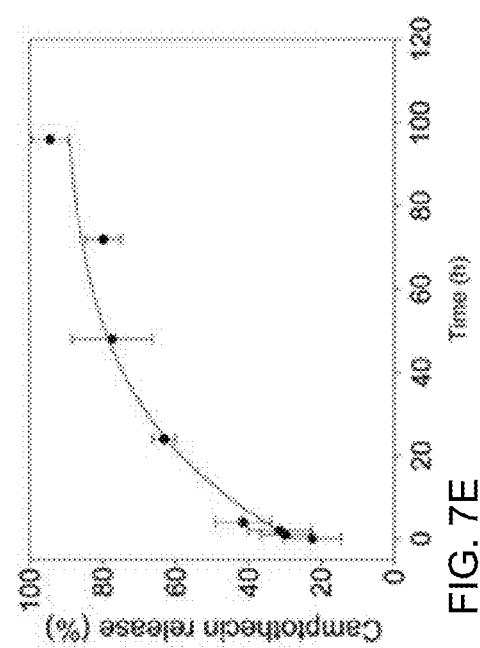
FIG. 7F
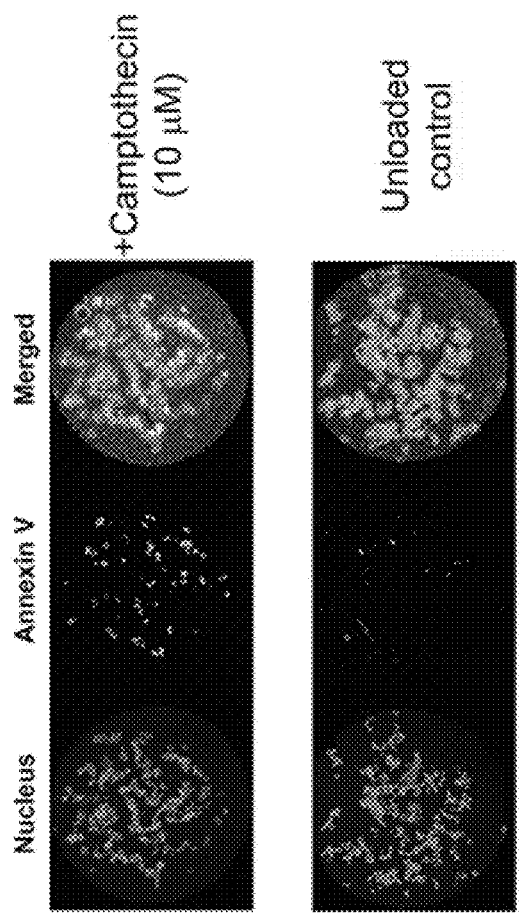
FIG. 7G
FIG. 7H

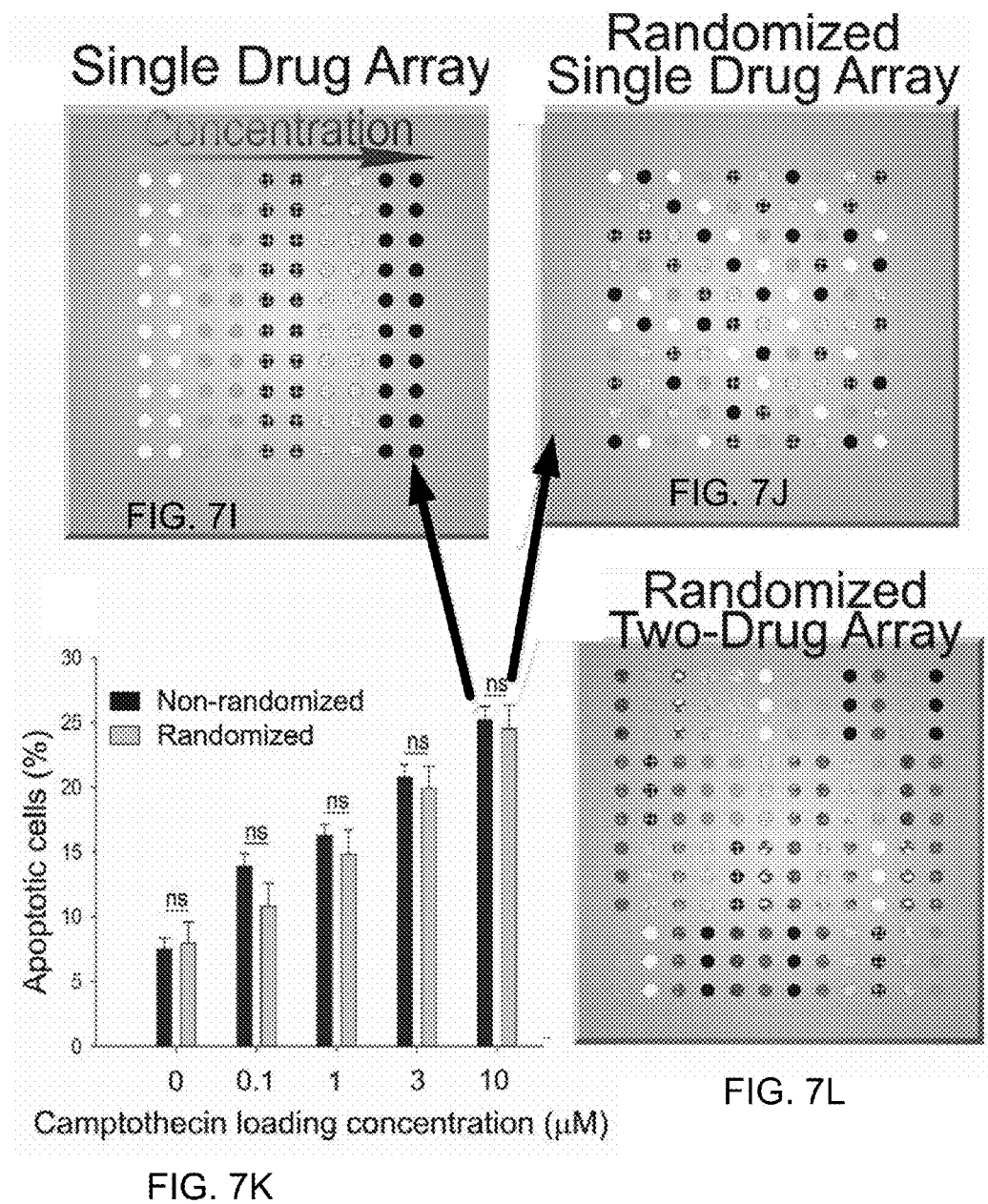

(Go To FIG. 10B-10I)

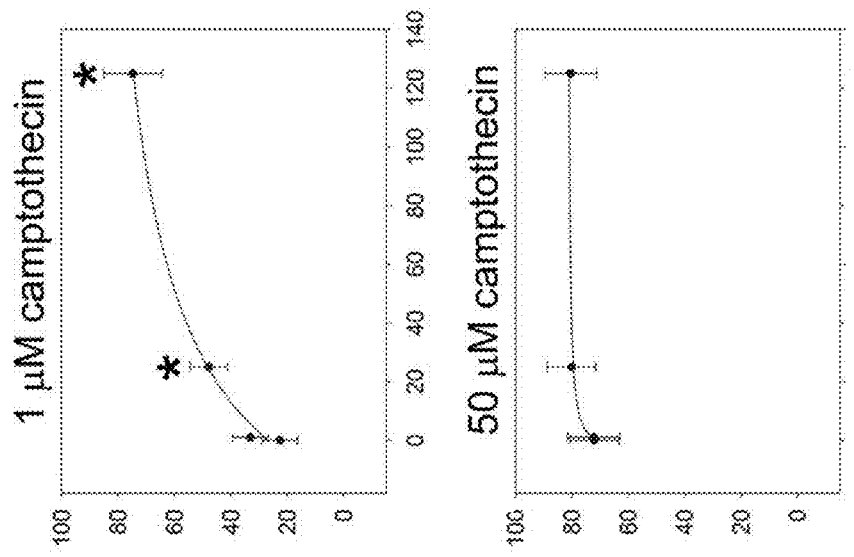
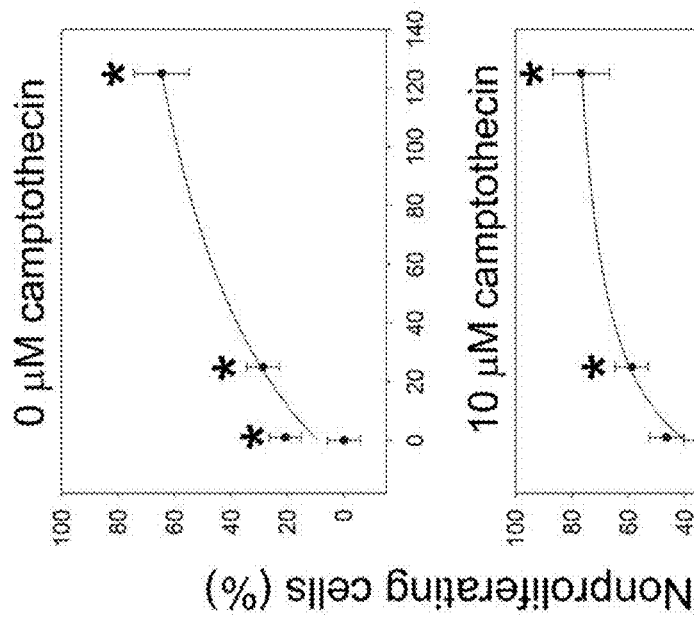

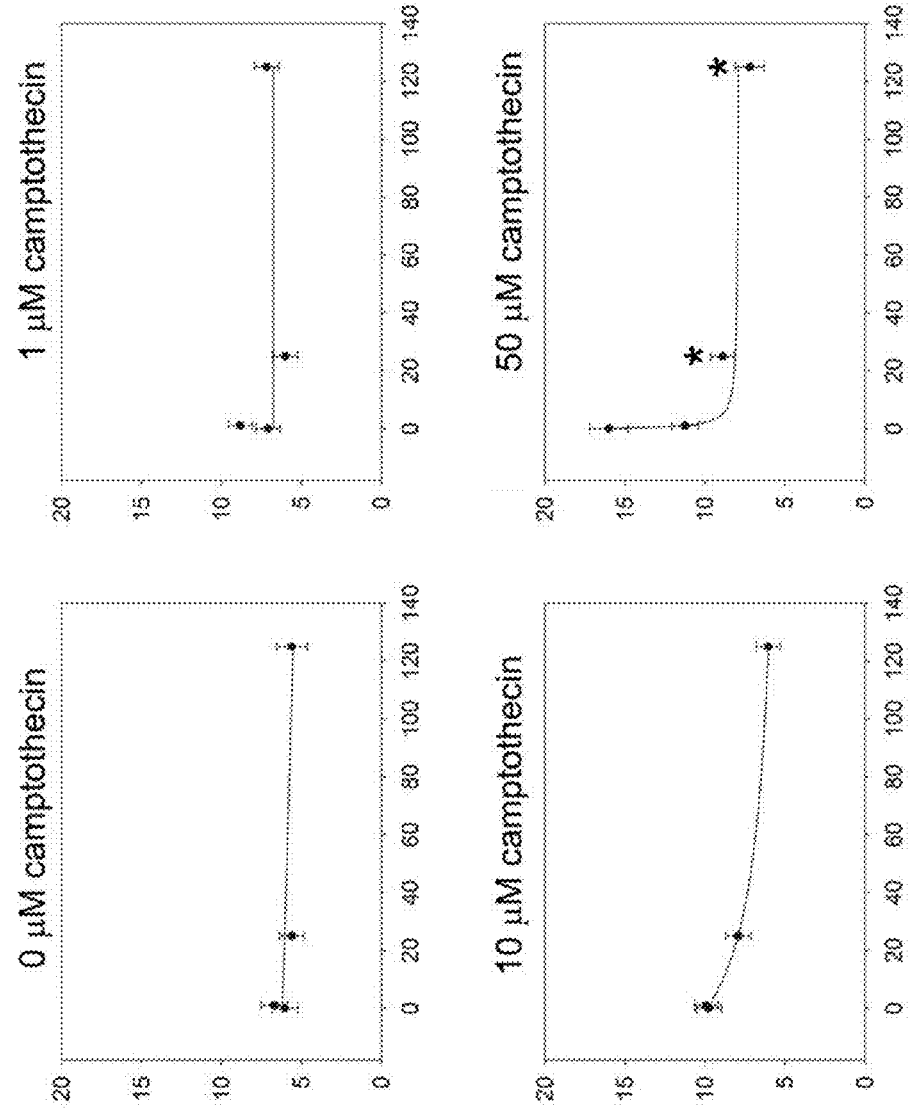

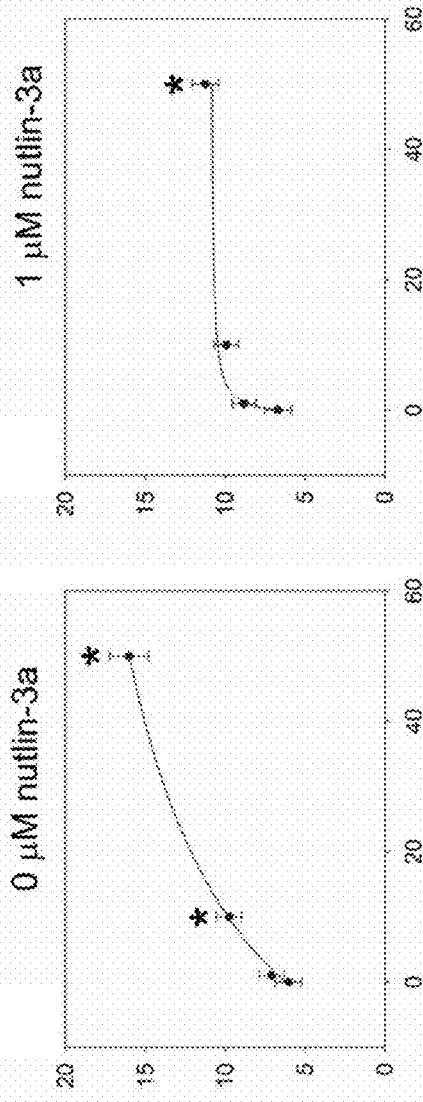

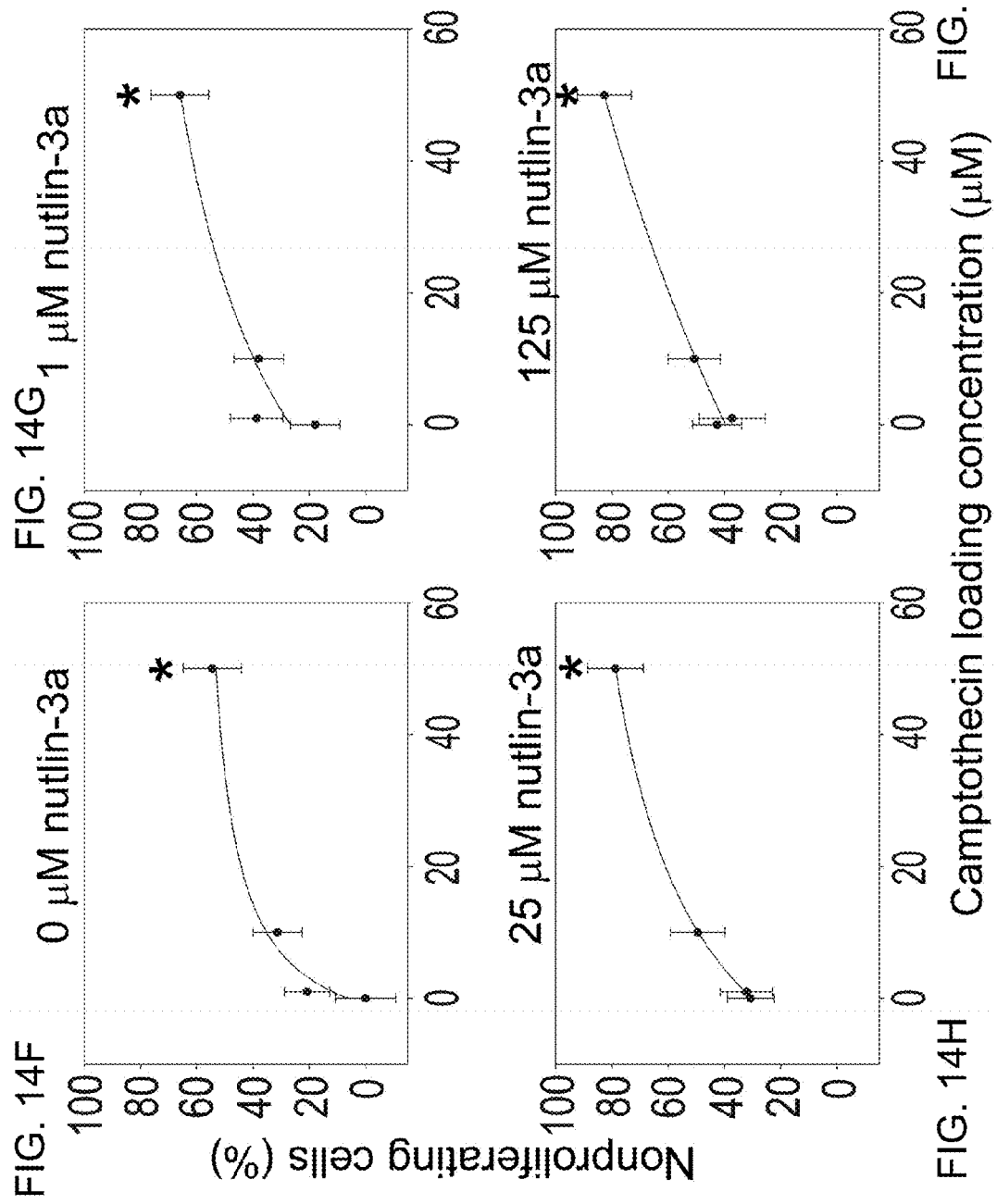

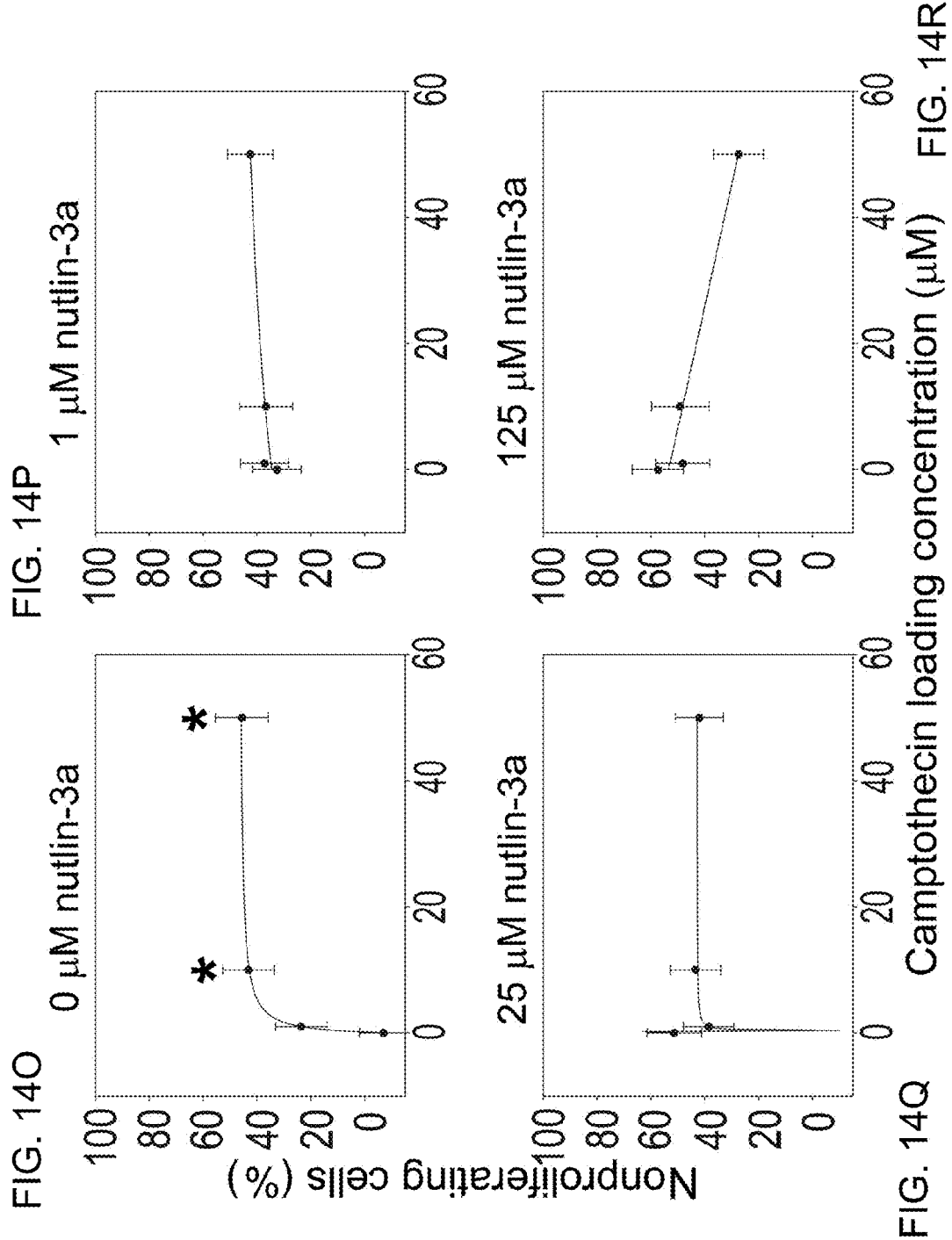

CELL-BASED ARRAYS, METHODS OF MAKING, AND METHODS OF USING

CROSS-REFERENCE TO RELATED APPLICATION

This application is a continuation-in-part application of and claims priority to U.S. patent application entitled "CELL-BASED ARRAYS, METHODS OF MAKING, AND METHODS OF USING," having Ser. No. 13/373,051 and filed on Nov. 2, 2011, which claims priority to U.S. provisional patent application of the same title having Ser. No. 61/409,223, filed on Nov. 2, 2010, both of which are entirely incorporated herein by reference. This application also claims priority to U.S. provisional patent application entitled "CELL-BASED ARRAYS, METHODS OF MAKING, AND METHODS OF USING," having Ser. No. 61/826,139 and filed on May 22, 2013, which is entirely incorporated by reference herein.

STATEMENT REGARDING FEDERALLY SPONSORED RESEARCH OR DEVELOPMENT

This invention was made with government support under grant No. DGE0802270 awarded by the National Science Foundation, and grant Nos. R21 AI094360, CA142808, and CA157663 awarded by the National Institutes of Health. The government has certain rights in the invention.

BACKGROUND

It is becoming increasingly evident in cancer treatment that simultaneously targeting multiple critical pathways, using combinations of chemotherapeutic drugs, can enhance outcome[1-5]. Currently, oncologists lack the tools necessary to predict the success of various combination treatments from one patient to the next. Sensitivity to different classes of chemotherapeutics is highly variable, due in part to intratumor heterogeneity[1]. Recent findings attribute this heterogeneity to a rare population of cancer stem cells (CSCs) which are now being targeted for therapy. A barrier to this approach is the limitation of having very few available cells on which to test drug combinations[6,7].

Colon cancer is the third most common cause of cancer and cancer death in the United States. Colon cancer stem cells (CCSC's) have only recently been recognized as a potential cause of colon cancer with several markers identified. As such, this cell population has also been targeted for future therapeutics, but the rarity of CCSC's makes it difficult to screen potential agents.

SUMMARY

Embodiments of the present disclosure provide for arrays, systems, and methods for analyzing cells, methods of making arrays, and the like.

An embodiment of the array, among others, includes: a non-fouling layer disposed in a first area of the array, where cells do not substantially adhere to the non-fouling layer; and a plurality of cell binding sites, each being disposed in a cell binding site area of the array distinct from the non-fouling layer, where the cell binding sites include a cell adhesion layer and a timed-release polymer layer, where each timed-release polymer layer corresponding to a cell binding site includes one or more types of an agent, where one or more types of target cells adhere to the cell adhesion layer, and where the timed-release polymer has the characteristic of releasing the agent to the cell or cells adhered to the cell binding site. The timed-release polymer layer of at least one cell binding site includes at least one type of agent different from at least one type of agent in the timed-release polymer layer of at least one other cell binding site or has a different concentration of agent than the concentration of agent in the timed-release polymer layer of at least one other cell binding site An embodiment of the array, among others, includes: a first substrate having a first area and a plurality of cell binding site areas, wherein the first area of the array includes: a first bonding layer disposed on the first area of the first substrate; a second bonding layer disposed on the first bonding layer; a non-fouling layer disposed on the second bonding layer, wherein cells do not adhere to the non-fouling layer; and wherein the cell binding site areas are different areas of the first substrate, wherein the cell binding site areas include: an adhesive layer disposed on each of the cell binding site areas of the first substrate; a timed-release polymer layer disposed on the adhesive layer; and a cell adhesion layer disposed on the timed-release polymer layer. In this embodiment, the timed-release polymer layer of at least one cell binding site includes at least one type of agent different from at least one type of agent in the timed-release polymer layer of at least one other cell binding site or has a different concentration of agent than the concentration of agent in the timed-release polymer layer of at least one other cell binding site Other structures, arrays, methods, features, and advantages of the present disclosure will be, or become, apparent to one with skill in the art upon examination of the following drawings and detailed description. It is intended that all such additional structures, methods, features, and advantages be included within this description, be within the scope of the present disclosure, and be protected by the accompanying claims.

BRIEF DESCRIPTION OF THE DRAWINGS

Many aspects of the disclosed devices and methods can be better understood with reference to the following drawings. The components in the drawings are not necessarily to scale, emphasis instead being placed upon clearly illustrating the relevant principles. Moreover, in the drawings, like reference numerals designate corresponding parts throughout the several views.

FIG. 1.1 illustrates a cross-section of an embodiment of the present disclosure.

FIG. 1.2 illustrates a cross-section through the a-a plane of the embodiment shown in FIG. 1.1.

FIG. 1.3A illustrates a schematic of an embodiment of the present disclosure, while FIG. 1.3B illustrates a representative microarray having more than 1000 spots.

FIG. 2.1 illustrates a phase micrograph of an array seeded with murine colon cancer stem cells.

FIGS. 2.2A to 2.2C illustrate micrographs of CCSC's attached to PLGA island imaged using Phase (FIG. 2.2A), DAPI (FIGS. 2.2A and 2.2B), and FITC (FIGS. 2.2A and 2.2C), respectively.

FIG. 2.3 is a graph that illustrates a release profile for PLGA films loaded with coumarin, 355 nm/460 nm.

FIG. 3.1 illustrates human epithelial cells (HCE-T corneal epithelial cells) that are shown seeded on a PLGA film array (over-spotted with adhesion molecules collagen and fibronectin).

FIG. 3.2 illustrates the release over time of coumarin (fluorescent dye) from a chip printed with 169 coumarin-loaded PLGA films.

FIG. 4.1 illustrates a phase contrast/fluorescence overlay micrograph displaying SW480 cells attached to isolated ethylene vinyl acetate (EVA) islands. Cells were seeded onto a small-molecule eluting array and stained with Hoechst 34580.

FIG. 4.2 illustrates a mosaic of SW480 cells seeded onto small-molecule eluting array and stained with Hoechst 34580.

FIG. 4.3 illustrates a micrograph of one column in 7×7 small-molecule-eluting cellular array separated by a fluorescent channel. Arrays were seeded with SW480 cells and stained for BrdU incorporation (green/middle column), indicating proliferating cells, and nuclear counter-stain (blue/left-hand column) (right-hand column shows both).

FIG. 4.4 illustrates a release profile from arrays printed with 20% (w/w) coumarin-loaded EVA. The upper curve (squares) represents arrays printed with single spots of coumarin-loaded EVA, while the lower curve (triangles) represents a blank EVA film printed over the coumarin-loaded EVA films to delay dye release.

FIGS. 5.1A to 5.1C illustrate HCT116 cells that are nuclear stained with Hoechst over a time of 5 h, 52 h, and 68 h, without any azide present.

FIGS. 5.2A to 5.2C illustrate HCT116 cells that are nuclear stained with Hoechst over a time of 5 h, 52 h, and 68 h, with 37.5 mM azide present.

FIGS. 5.3A to 5.3C illustrate HCT116 cells that are nuclear stained with Hoechst over a time of 5 h, 52 h, and 68 h, with 75 mM azide present.

FIGS. 5.4A to 5.4C illustrate HCT116 cells that are nuclear stained with Hoechst over a time of 5 h, 52 h, and 68 h, with 75 mM azide present.

FIG. 6A is a schematic illustration of printing of glass coverslips to form the arrays. FIG. 6B shows a schematic of a single spot highlighting the substrate architecture, the chemistry of the non-fouling PEG coating, and the drug eluting polymer with cells attached (not to scale). FIG. 6C is a fluorescence microscopy mosaic image of a 10×11 microarray seeded with HCT116 colon carcinoma cells illustrating fidelity of cell adhesion to isolated islands of drug-eluting polymer films. Also shown is a detail of a single drug eluting island demonstrating adherent cells (nuclear staining is highlighted/outlined in lighter shading). Scale bar=200 µm.

FIGS. 7A-7L illustrate cumulative drug release from array spots and HCT116 cell responses to drug-loaded microarrays. FIG. 7A is a graph illustrating nutlin-3a release profile from microarray revealed a burst release of approximately 8 h followed by a steady release rate over five days. Release profiles show means±standard deviations of three replicates, and data is modeled using exponential decay. FIG. 7B is a graph illustrating that the percent of non-proliferative HCT116 cells on nutlin-3a loaded microarray increases with increasing drug loading concentration. (Proliferation was quantified via BrdU incorporation and data is normalized to unloaded control. Significant differences were determined by ANOVA, $\{F(4,138)=19.068, p<0.05\}$, followed by Tukey's post-hoc analysis.) The images in FIG. 7C illustrates representative fluorescence micrographs of non-proliferating cells on a 25 µM nutlin-3a-loaded polymer island (low BrdU staining). FIG. 7D is an image illustrating representative fluorescence micrographs of an unloaded control island with highly proliferative cells (high BrdU staining). FIG. 7E is a graph illustrating the camptothecin release profile from microarray revealing a burst release of approximately 24 h followed by a steady release rate over five days. (Release profiles show means±standard deviations of three replicates, and data is modeled using exponential decay.) FIG. 7F is a graph illustrating that the percent of apoptotic cells on camptothecin loaded microarray increases with increasing drug loading concentrations. (Apoptosis was quantified by annexin V staining and significant differences were determined by ANOVA, $\{F(4,479)=52.778, p<0.05\}$, followed by Tukey's post-hoc analysis.) FIG. 7G shows representative fluorescence micrographs displaying high levels of cells undergoing apoptosis on a 10 µM camptothecin-loaded polymer island (high annexin V staining). The images of FIG. 7H illustrate representative fluorescence micrographs of an unloaded control island with low levels of apoptotic cells (low annexin V staining). FIG. 7I is a schematic illustration of a single factor dosing array layout with increasing drug loading concentrations. The schematic of FIG. 7J illustrates a randomized single factor array with loading concentrations configured in randomized fashion. The graph of FIG. 7K illustrates statistical comparison of cell apoptosis between the array configurations of FIGS. 7I and 7J and indicates results are independent of array configuration (n=3). This indicates that there is negligible cellular cross-talk or drug interaction between neighboring islands. FIG. 7 is a schematic illustration of a randomized two-factor dosing array used in combinatorial microarrays. Different patterns represent the 16 different combinations of two drugs (four concentrations per drug). (*: $p<0.05$ compared to all other conditions, #: $p<0.05$ compared to control). Scale bar=200 µM.

FIGS. 10A-I illustrate proliferation and dose-response curves from combinatorial microarrays of HCT116 cells. FIG. 10A is a three-dimensional graph illustrating that increasing concentrations of combination treatments increased the overall antiproliferative activity. Following 24 h incubation with both nutlin-3a and camptothecin, proliferation of HCT116 cells significantly decreased. A significant primary effect on proliferation relative to nutlin-3a, $\{F(3,619)=18.253, p<0.01\}$, and camptothecin, $\{F(3,619)=25.056, p<0.01\}$ was revealed by two-way ANOVA. Additionally, a sub-additive effect was observed from combination treatments. The graphs in FIGS. 10B-10E illustrate dose response curves of fixed camptothecin concentrations with variable nutlin-3a concentration. The addition of camptothecin increased the sensitivity to nutlin-3a by over 5-fold (19.6 for 50 µM CPT compared to 3.0 for 0 µM CPT). The graphs in FIGS. 10E-10I illustrate dose response curves of fixed nutlin-3a concentrations with variable camptothecin concentration. The presence of nutlin-3a increased the sensitivity to camptothecin by over 16-fold (78.1 for 125 µM nutlin compared to 4.83 for 0 μM nutlin). Proliferation data were transformed to non-proliferation data by subtracting the former from 100%. (*: $p<0.05$ compared to 0 drug) (Bars atop columns represent SEM).

FIGS. 11A-11I illustrate apoptosis and dose-response curves from combinatorial microarrays of HCT116 cells. FIG. 11A is a three-dimensional graph illustrating that Nutlin-3a and camptothecin had varying effects on inducing apoptosis of HCT116 cells. A significant antagonistic effect on apoptosis was observed from combination treatments as revealed by two-way ANOVA, $\{F(9,342)=3.371, p<0.05\}$. FIGS. 11B-11E illustrate dose response curves of fixed camptothecin concentrations with variable nutlin-3a concentration. The graphs of FIGS. 11C-11E illustrate that increasing the nutlin-3a concentration conferred protection from the apoptotic response to camptothecin. FIGS. 11F-11I are graphs showing a dose response curve of fixed nutin-3a concentrations with variable camptothecin concentration. The graphs of FIGS. 11G-11I illustrate that addition of nutlin-3a attenuated the apoptotic response to camptothecin. Sensitivity could not be statistically compared when evaluating apoptosis as the hyperbolic curve fit does not apply to the linear dose response curves. (*: $p<0.05$ compared to 0 μM) (Bars atop columns represent SEM).

FIG. 12A illustrates the percent of apoptotic HCT116 cells incubated 24 h with soluble nutlin-3a. FIG. 12B shows the percent of apoptotic HCT116 cells incubated 24 h with soluble camptothecin. Significant differences were determined by ANOVA, $\{F(5, 282)=19.694, p<0.05\}$, followed by Tukey's post-hoc analysis. FIG. 12C illustrates the percent of non-proliferating HCT116 cells incubated 24 h with soluble nutlin-3a. Significant differences were determined by ANOVA, $\{F(4, 226)=12.643, p<0.05\}$, followed by Tukey's post-hoc analysis. FIG. 12D shows the percent of non-proliferating HCT116 cells incubated 24 h with soluble camptothecin. Significant differences were determined by ANOVA, $\{F(5, 252)=102.485, p<0.05\}$, followed by Tukey's post-hoc analysis. (*: $p<0.05$ compared to all other conditions, #:$p<0.05$ from all conditions marked *).

FIG. 13A shows that ALDH (a marker for CCSCs) expression was unchanged in cells from CA1 when cultured as spheres or monolayers, whereas cells from CA2 showed markedly decreased expression of ALDH when cultured as monolayers compared to spheroids. FIG. 13B shows that MUC2 (a marker for goblet cell lineage) expression decreased slightly in cells from CA1 when cultured as monolayers compared to spheroids. By contrast, cells from CA2 showed higher MUC2 expression in monolayers versus spheroid culture.

FIGS. 14A-14R illustrate patient-derived CCSC responses to drug-loaded microarrays. FIG. 14A is a three dimensional graph illustrating proliferation response of CA1 cells on drug-eluting cellular microarrays. FIGS. 14B-14I are graphs showing dose responses of CA1 cells exposed to ranges of one drug in combination with a fixed amount of a second drug. Proliferation values were transformed to non-proliferation by subtracting values from 100%. FIGS. 14K-14R illustrate dose responses of CA2 cells exposed to ranges of one drug in combination with a fixed amount of a second drug. Proliferation values were transformed to non-proliferation outcomes by subtracting values from 100%. (*: $p<0.05$ from 0 μM). (Bars atop columns represent SEM).

DETAILED DESCRIPTION

Figure 6A:
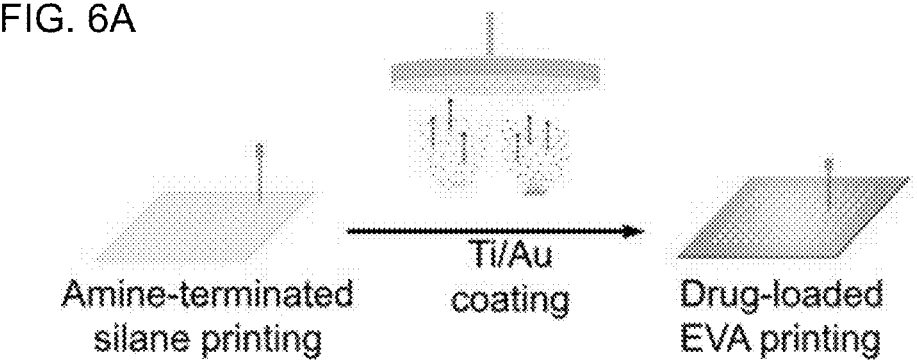
FIGS. 6A-6C illustrate an embodiment of drug-eluting cellular microarrays of the present disclosure.

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

Publications and patents cited in this specification are incorporated by reference where indicated and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, biochemistry, biology, molecular biology, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

In accordance with the present disclosure there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984), each of which is incorporated herein by reference.

Use of the term "affinity" can include biological interactions and/or chemical interactions between or among a material (e.g., a compound or bio-molecule (e.g., polypeptide or polynucleotide)) and a cell. The biological interactions can include, but are not limited to, bonding or hybridization among one or more biological functional groups of the compound or cell. The chemical interaction can include, but is not limited to, bonding among one or more functional groups (e.g., organic and/or inorganic functional groups) located on the compound of cells.

The term "array" encompasses the term "microarray" and refers to an ordered array presented for binding to polynucleotides and the like.

An "array" includes any two-dimensional or substantially two-dimensional (as well as a three-dimensional) arrangement of addressable regions including nucleic acids (e.g., particularly polynucleotides or synthetic mimetics thereof) and the like. Where the arrays are arrays of polynucleotides, the polynucleotides may be adsorbed, physisorbed, chemisorbed, and/or covalently attached to the arrays at any point or points along the nucleic acid chain.

A substrate may carry one, two, four or more arrays disposed on a front surface of the substrate. Depending upon the use, any or all of the arrays may be the same or different from one another and each may contain multiple spots or features. A typical array may contain one or more, including more than two, more than ten, more than one hundred, more than one thousand, more ten thousand features, or even more than one hundred thousand features, in an area of less than about 20 $cm^2$ or even less than about 10 $cm^2$ (e.g., less than about 5 $cm^2$, including less than about 1 $cm^2$ or less than about 1 $mm^2$ (e.g., about 100 $\mu m^2$, or even smaller)). For example, features may have widths (that is, diameter, for a round spot) in the range from about 10 $\mu m$ to 1.0 cm. Non-round features may have area ranges equivalent to that of circular features with the foregoing width (diameter) ranges.

An array "package" may be the array plus a substrate on which the array is deposited, although the package may include other features. It will also be appreciated that, throughout the present application, words such as "top," "upper," and "lower" are used in a relative sense only.

An array, such as those described herein, is "addressable" when it has multiple regions of different moieties (e.g., cell binding sites) such that a region at a particular predetermined location (i.e., an "address") on the array can detect a particular outcome for a particular cell type and/or agent, interaction. Array features are typically, but need not be, separated by intervening spaces.

A "scan region" refers to a contiguous (preferably, rectangular) area in which the array features of interest (cell binding sites), as defined above, are found or detected.

An "array layout" refers to one or more characteristics of the features, such as feature positioning on the substrate, one or more feature dimensions, and an indication of a moiety at a given location.

Discussion

In accordance with the purpose(s) of the present disclosure, as embodied and broadly described herein, embodiments of the present disclosure, in one aspect, relate to arrays, systems, and methods for analyzing cells, methods of making arrays, and the like. In particular, embodiments of the present disclosure include an agent-delivering cell-based array (e.g., microarrays) that can be used to analyze the timed-release delivery of the agent (e.g., drug(s)) to cells such as rare cells (e.g., cancer cells, stem cells, precancerous cells, and the like), any patient-derived cells, or other rare or low population cells.

Analyzing chemosensitivity on an established panel of cancer cell lines is the conventional method to screening chemotherapeutics[8]. An emerging strategy in cancer treatment involves performing in vitro chemosensitivity testing of tumor biopsies as a predictive procedure to individualize chemotherapy treatments[9]. Benefits to date have been limited due to apparent poor correlations between in vitro sensitivity and in vivo responses. Traditional chemotherapeutic drugs are designed to target the rapidly dividing cells of the bulk tumor in vivo, or transformed cell lines derived from the bulk, in vitro. However, tumors include multiple phenotypes, due in part to the presence of CSCs[10,6,7]. In the CSC model, these tumor-initiating cells perpetually self-renew and give rise to tumor heterogeneity, metastasis, and disease recurrence[11,12]. Recent identification of unique cell surface markers that enrich colon-cell isolates for CSCs have led to techniques for isolating enriched CCSC populations from patient tumor samples[13-18]. After transplantation of a single CCSC enriched for high Wnt signaling activity, tumors have been generated that recapitulate the diverse phenotypic heterogeneity of the original tumor[17]. Thus, isolating and identifying CCSCs from an individual cancer patient and determining their sensitivity to chemotherapeutic drugs in vitro is possible and could potentiate personalized treatment of cancer[18,19].

While promising, cell source limitations make targeting CSCs for treatment problematic. CSCs with the greatest tumor-initiating and metastatic potential are exceptionally rare (~1% of tumor cells), making them difficult to isolate. Moreover, the time required for gold standard methods of CSC isolation and propagation makes it impractical to develop individualized therapy using traditional screening methods which require large quantities of cells. The methods and systems embodied in the present disclosure address these challenges with a device and methods capable of facilitating personalized chemosensitivity screening.

Embodiments of the present disclosure can permit multiple different biological or pharmaceutical agents and combinations thereof to be tested on rare cell populations. Cell binding sites that include a thin film(s) or layer(s) of timed-released polymer, loaded with an agent(s) of interest, are microarrayed onto a substrate, where the substrate includes a non-fouling layer or background around the cell binding sites that resists or prevents cell adhesion to the non-fouling layer on areas excluding the cell binding sites. Each cell binding site is able to provide a unique agent or combination of agents to be released. In addition, a thousand spots or more may be arrayed onto a single substrate (e.g., standard glass slide).

An embodiment of the array can be implemented with the seeding of a rare cell population of interest onto the array, requiring relatively less cells than alternative systems such as microwell plates and/or microfluidics systems. Non-adherent cells can be removed, thereby providing isolated islands of adherent cells disposed on the cell binding sites in close contact with the timed-release polymer that includes the agent. Outcome parameters of cellular response, including, but not limited to, proliferation, apoptosis, and differentation using defined agonists/antagonists, are able to be determined through immunostaining or use of a contrast agent, in multiple concentrations of one or more combinations of agents, in the assay. Multiple conditions (e.g., one or more agents in the timed-release polymer, different agents at different cell binding sties, different concentrations of agents at different cell binding sites, and the like) can be evaluated simultaneously using simple common laboratory protocols (with a limited cell number, and without the use of expensive automated microfluidics machines) with application toward personalized medicine (i.e., focused screening of drug interactions with rare cell populations from patients, for example diagnostics for cancer stem cells). Embodiments of this array would lower expenses since fewer reagents/cells would be required, thereby increasing throughput and productivity. These increases would result in more rapid diagnostic capacity.

In an embodiment shown in FIG. 1.1, the array 2 includes a non-fouling layer 4 disposed in a first area of the array 2. The array 2 also includes a plurality of cell binding sites 6. Each of the cell binding sites 6 is disposed in a cell binding site area of the array 2 that is distinct from the non-fouling layer 4. In other words, the non-fouling layer and the cell binding sites areas are separate and distinct areas. Each of the cell binding sites 6 can have an area of about 20 $\mu m^2$ to 5 $mm^2$, where each cell binding site 6 does not have to have the same area. In an embodiment, the area of each cell binding site 6 can be polygonal, circular, semicircular, a combination thereof, or amorphous. Each area of the cell binding site 6 can have the same shape, a combination of shapes, or different shapes. The cell binding sites 6 can be positioned a distance (e.g., about 10 $\mu m$ to 2 mm or more) from one another so that cross-talk or other interference is substantially reduced or is not exhibited. An array 2 can include a few (e.g., 2, 3, 4, 5, 6, 10, 20, 50, 100, and the like) cell binding sites 6 to a 1000 or more cell binding sites 6 in an area of about 100 $\mu m^2$ to 1,800 $mm^2$, or more for larger array substrates.

Each of the cell binding sites 6 includes a cell adhesion layer 28 and a timed-release polymer layer(s) 26 (additional details provided below). Each timed-release polymer layer 26 corresponding to a cell binding site 6 includes one or more types of an agent (e.g., drug, biological, or other agent that can be tested as to its affect on the cell). One or more types of target cells can adhere to the adhesion layer 28. Cells that are not adhered to the cell binding sites 6 can be removed, so only cell binding sites 6 have target cells adhered thereto since the non-fouling layer 4 eliminates or substantially (e.g., about 80%, about 90%, about 95%, about 99%, or about 99.9% or more, in particular about 95% or more) eliminates non-target cells adhering to it.

In an embodiment, the interaction between the cell and the cell binding sites can include electrostatic interactions, van der Waals interactions, hydrogen bonding, hydrophobic interactions, or a combination thereof. In an embodiment, the interaction between the cell and the cell binding sites can also be bound through specific biological binding, covalent binding, and/or entrapment in a gel (e.g., PEG hydrogel, fibrin gel, collagen gel, etc.).

Once the non-adhered cells are removed, the adhered target cells can be exposed over time (e.g., hours to days to weeks) to the agent released from the timed-release polymer layer 26. The effect of the agent on the cells can be studied and analyzed as a function of time. In addition, the effect of the agent on the cells can be studied and analyzed as a function of agent type, combinations of agents, concentrations of agent(s), and the like.

In an embodiment, the target cell of interest may not adhere to a known compound or bio-molecule, but may adhere to another cell type (e.g., fibroblasts, epithelial cells). One way to analyze the target cell is to first adhere a cell that adheres to the target cell to the cell binding site 6. Then the un-adhered cells can be removed, and the target cell of interest can be introduced to the array so that the target cell of interest adheres to the cell on the cell binding site 6. In other words, the cell binding site 6 has a first cell type bonded to the adhesion surface layer 28 and the target cell of interest is adhered to this cell. In another embodiment, the two cells are adhered to one another prior to introduction to the array, and then the cell that adheres to the cell adhesion layer becomes disposed on the cell binding site. In embodiments the target cell is a cancer stem cell (CSC) or other rare cell type, and in embodiments the CSC is a colorectal cancer stem-like cell (CCSC).

FIG. 1.2 is a cross-section of an array illustrating one cell binding site (a-a plane shown in FIG. 1.1). FIG. 1.3A illustrates a schematic of an embodiment of the present disclosure, while FIG. 1.3B illustrates a representative microarray having more than 1000 spots.

As shown in FIG. 1.2 the array includes a substrate 12 having a first area and a cell binding site area. The first area and the cell binding site areas are different and distinct areas of the first substrate 12. A first bonding layer 14 is disposed on the first area of the first substrate 12. A second bonding layer 16 is disposed on the first bonding layer 14. In an embodiment, one could combine the first bonding layer 14 and the second bonding layer 16 into a single bonding layer. In an embodiment, the non-fouling layer 18 and 22 can be formed of two layers and they are disposed on the second bonding layer 16. In an embodiment, the non-fouling layer 18 and 22 can be attached directly to the substrate 12. An adhesive layer 24 is disposed on each of the cell binding site areas of the first substrate 12. The timed-release polymer layer 26 is disposed on the adhesive layer 24. The cell adhesion layer 28 is disposed on the timed-release polymer layer 26.

The substrate 12 enables imaging live cells and fixed cells, e.g., via brightfield or fluorescence microscopy. In an embodiment, the substrate 12 can be a rigid and optically transparent substrate. In an embodiment, the substrate 12 can be glass (e.g. mica, Pyrex®, and the like); PET, polycarbonate, styrene, and other amorphous polymers; silicon wafer; quartz; and the like. In an embodiment, the substrate 12 can have a thickness of about 0.05 mm to 10 mm. The area of the substrate 12 can vary depending on the desired number of cell binding sites, the distance between the cell binding sites, the size of the cell binding sites, and the like. In an embodiment the area is about 10 mm$^2$ to 1,800 mm$^2$.

The first bonding layer 14 provides a bonding construct for the substrate 12 and the second bonding layer 16. In an embodiment, the first bonding layer 14 can be titanium, nickel, chromium, and the like. The first bonding layer 14 can have a thickness of about 1 nm to 500 nm.

The second bonding layer 16 provides a surface for alkanethiols to form bonds for formation of self-assembled monolayers. In an embodiment, the second bonding layer 16 can be gold, silver, copper, palladium, platinum, nickel, and alloys of any of these. The second bonding layer 16 can have a thickness of about 1 nm to 500 nm.

In an embodiment, the first and second bonding layer could be a single layer that achieves both the functions of the first bonding layer 14 and the second bonding layer 16.

The non-fouling layer (or surface) functions to resist, prevent, or substantially prevent cell attachment in the area that the non-fouling surface is disposed. In an embodiment, the non-fouling layer can be made up of two layers, 18 and 22. In another embodiment, the non-fouling layer can be made of a single layer or multiple layers that achieve the same function as the first layer 18 and the second layer 22.

The first non-fouling layer 18 functions to attach to the second bonding layer 16. In an embodiment, the first non-fouling layer 18 can be made of self-assembled monolayer of methyl-terminated alkanethiol—treatment to promote adsorption of pluronic; hydrophobic polymers (e.g., polyethylene, polyethylene terephthalate, siloxanes); non-polar peptides/amino acids (e.g., alanine, leucine, valine, isoleucine); micro/nano textures; and the like. The first non-fouling layer 18 can have a thickness of about 1 nm to 100 nm.

The second non-fouling layer 22 is attached to the first non-fouling layer 18 and can resist attachment by cells. In an embodiment, the second non-fouling layer 22 can be made of glycol-based polyethylene; a neutral polymer (e.g., poly (2-hydroxyethyl methacrylate, polyacrylamide, poly(N-vinyl-2-pyrolidone, and poly(N-isopropyl acrylamide) (below 31° C.))); an anionic polymer; a phosphoryl choline polymer; gas discharge-deposited coatings (especially from PEG-like monomers); self-assembled n-alkyl molecules with oligo-PEG head groups; self-assembled n-alkyl molecules with other polar head groups; passivating proteins (e.g., albumin and casein); polysaccharides (e.g., hyaluronic acid); liposaccharide; phospholipid mono/bilayers (e.g., phosphorylcholine); glycoproteins (e.g., mucin), and the like. The second non-fouling layer 22 can have a thickness of about 1 nm to 20 µm.

The adhesive layer 24 provides a surface for the timed-release polymer layer 26 and attaches to the substrate 12. In an embodiment, the adhesive layer 24 can be a silane; chemical groups forming covalent bonds to polymer such as: ethylene oxide, acrylamide, other crosslinking schemes; chemical groups promoting non-specific interactions (electrostatic, hydrophobic, van der Waals) such as amine groups (e.g., the amine-terminated silane depicted, polylysine, polyethyleneimmine) or hydrophobic groups (e.g., methyl-terminated silane) or micro/nanotextures; and the like. The adhesive layer 24 can have a thickness of about 1 nm to 500 nm.

The timed-release polymer layer 26 functions to delivers drugs (or agents) and in some instances can promote cell adhesion. In an embodiment, the timed-release polymer layer 26 can be a poly(lactic-co-glycolic acid); polycaprolactone; polyglycolide; polylactic acid; poly(vinylpyridine); chitosan; alginate; and the like. The timed-release polymer layer 26 can have a thickness of about 10 nm to 5 µm. In an embodiment, the timed-release polymer layer 26 can include a plurality of layers each having a thickness of about 10 nm to 5 µm. In an embodiment, the additional layers can function to increase the time that the agent is delivered. In addition to or in the alternative to the timed-release polymer layer 26, the drugs (or agents) can be bound and/or tethered to the one or more layers of the cell binding site to achieve the same function of the timed-release polymer layer. In an embodiment, the cellular uptake can process through a process such as phagocytosis.

The agents can be used to test, study, analyze, and the like, outcomes of the interaction of the agent with the cell. The concentration of the agents can be varied between or among the timed-release polymer layers of the array. Advantages to the arrays and methods of the present disclosure include the ability to test various different agents (e.g., drugs), agent concentrations, and combinations on a single array without having to use a large amount of target cells. In embodiments various agents can be combined in different combinations in the timed-release polymer layers of each cell binding site, such that multiple cell binding sites have different agents present in combination with other agents in various concentrations. In embodiments, the timed-release polymer layer for each cell binding site is prepared to have one or more drugs in one or more different concentrations or combinations of concentrations. For instance, the timed-release polymer layer of at least one cell binding site can include at least one type of agent different from at least one type of agent in the timed-release polymer layer of at least one other cell binding site. Similarly, the timed-release polymer layer of at least one cell binding site can include a first concentration of one type of agent different from a concentration of that type of agent in the timed-release polymer layer of at least one other cell binding site. In embodiments, different cell binding sites include both different agents and different concentrations or combinations of agents that other cell binding sites. In embodiments, multiple cell binding sites have one or more different types of agent in the timed-release polymer layer than the types of agent in the timed-release polymer layers of other cell binding sites. Similarly, multiple cell binding sites have one or more different types of agents or combinations of agents present in different concentrations than the types and combinations of agents in the timed-release polymer layers of other cell binding sites. Thus, one or more or a plurality of agents can be present in each cell binding site in different concentrations and combinations with other agents to test different combinations of agents in different amounts on the target cells. In embodiments, the array includes at least a first and second type of agent, where the first agent is present in at least two different concentrations in the timed-release polymer layers of at least two different cell binding sites and the second agent is present in at least two different concentrations in at least two different cell binding sites, and where the first agent and second agent are combined in different concentrations in at least two different cell binding sites. The agents can include drugs, compounds, bio-molecules, and the like. In embodiments, one or more agents can be selected from nutlin-3a, camptothecin, and combinations of those agents.

The cell adhesion layer 28 functions to promote adhesion of the cells to the cell binding site by capturing the cells so that the agent can be delivered to the cells. The cell adhesion layer 28 has an affinity for one or more types of cells such as tumor initiating cells, stem cells, inflammatory/immune cells, hematologic cellular components, neural cells, microenvironmental cellular elements, and the like. In an embodiment, the cell adhesion layer 28 can promote adhesion of a specific cell type(s) or can be a material that promotes non-specific binding (e.g., positively-charged treatments such as polylysine, polyethyleneimmine). In an embodiment the cell adhesion layer 28 can include: fibronectin (e.g., endothelia); polylysine (e.g., epithelia); collagen (e.g., epithelia); vitronectin (e.g., fibroblasts); intercellular adhesion molecules (ICAM-1,2,3,4,5); immunoglobulin superfamily Cell Adhesion Molecules (IgSF CAMs) (e.g., dSynCAMs Synaptic Cell Adhesion Molecules (e.g., epithelia), NCAMs Neural Cell Adhesion Molecules (e.g., neural cells), ICAM-1 Intercellular Cell Adhesion Molecule (e.g., leukocytes), VCAM-1 Vascular Cell Adhesion Molecule (e.g., leukocytes), PECAM-1 Platelet-endothelial Cell Adhesion Molecule (e.g., platelets), L1, integrin (e.g., leukocytes); cadherin (e.g., epithelia); and the like. In an embodiment, the cell adhesion layer 28 can have a thickness of about 0.2 nm to 2 μm.

As described above, methods of the present disclosure can include separating cells (e.g., rare cells) from other cells using an array of the present disclosure. Subsequently, the captured cells can be exposed to an agent. In addition, embodiments of the present disclosure include systems using an array of the present disclosure to capture and analyze cells, where the system includes the array and equipment to introduce, remove, etc., reagents and the like.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

As noted above, CCSC's are rare and therefore it is difficult to screen potential agents. In this example we provide an array that can be used to analyze CCSC's (e.g., FIG. 1.3A) using a limited number of cells. This technique utilizes arrays of spotted PLGA films loaded with signaling pathway inhibitors. Signaling pathways govern self-renewal and as such have been identified as a target for therapy. The selected factors include KAAD-Cyclopamine, a sonic hedgehog antagonist; DKK-1, a WNT inhibitor; Compound E, a notch pathway antagonist; and rapamycin, an a mTOR inhibitor; Various concentrations were used and factors were printed in randomized arrays in order to factor out potential cross-talk between arrayed spots. Colon stem cells, both cancerous and precancerous, were isolated using ALDH and CD44 expression and identified by cytokine array analyses. Cells were seeded onto colon stem cell inhibitor microarrays, cell attachment was assessed through DAPI staining and proliferation quantified by immunostaining for BrdU incorporation. This example shows that a microarray platform has been developed that allows for a systematic investigation of the role of signaling pathway inhibitors on the response of CCSC's isolated from murine colon crypts, requiring limited cell numbers.

FIG. 2.1 illustrates a phase micrograph of an array seeded with murine colon cancer stem cells. FIGS. 2.2A to 2.2C illustrate micrographs of CCSC's attached to a PLGA island imaged using Phase (FIG. 2.2A), DAPI (FIGS. 2.2A and 2.2B), and FITC (FIGS. 2.2A and 2.2C). FIG. 2.3 is a graph that illustrates a release profile for PLGA films loaded with coumarin, 355 nm/460 nm.

The array can be fabricated using oxygen plasma cleaned coverslips printed with silane in specific array formats. Printed coverslips were coated with 175 Å of titanium followed by 250 Å of gold. Gold coated coverslips were sonicated to expose silane islands. The coverslips were then incubated with methyl-terminated alkanethiol followed by 10% pluronic F-127 to create a nonfouling background. Appropriate drug concentrations were loaded into 10% poly(D,L lactide-co-glycolide) (PLGA) dissolved in polycarbonate. The following drugs were used: Rapamycin—mTOR inhibitor; DKK1—WNT inhibitor; KAAD—Sonic hedgehog inhibitor; Compound E—Notch pathway antagonist; and Wortmannin—P13K. Cell adhesion molecules are then over spotted onto PLGA film islands.

The method of isolating colon cancer stem cell is described below. Colon cancer xenografts were dissociated and colon stem cells, both cancerous and precancerous, were isolated using ALDH, CD44, and ESA expression and identified by cytokine array analyses. Cells are seeded onto array, allowed to attach specifically to islands, and pulsed with BrdU. After 24 h, samples were fixed and stained. Fluorescence and phase contrast micrographs were then taken.

Example 2

Human epithelial cells (HCE-T corneal epithelial cells—representative of an adherent cell type that could be tested) are shown seeded on a PLGA film array (over-spotted with adhesion molecules collagen and fibronectin) (FIG. 3.1). Seeding density was 1 million cells in 3 ml serum-free media, seeding time was approximately 10 minutes, followed by washing to remove loosely-adherent cells from the non-fouling PEG background.

Shown is the release over time of coumarin (fluorescent dye—representative of a small hydrophobic molecule such as many drugs) from a chip printed with 169 coumarin-loaded PLGA films (FIG. 3.2). Characteristics of interest are a burst release within the first 24 hr followed by a more linear release over the next 5 d. These release characteristics are in line with other configurations of PLGA-loaded delivery vehicles (e.g., microparticles, wafers) and are amenable to the cellular array device.

Example 3

FIG. 4.1 illustrates a phase contrast/fluorescence overlay micrograph displaying SW480 cells attached to isolated ethylene vinyl acetate (EVA) islands in a similar manner to methods described for FIG. 3.1 however with a different cell line and different drug-releasing polymer. This is a close-up image of an array similar to that shown in FIG. 4.2. SW480 cells are a human colorectal adenocarcinoma line which are epithelial like in morphology and used as an in vitro model for colorectal cancer. Cells were seeded onto small-molecule eluting array and stained with nuclear stain (blue).

FIG. 4.2 illustrates a whole 11×13 array of SW480 cells seeded onto small-molecule eluting array and stained with nuclear stain (blue). This figure illustrates high specificity of cell adhesion onto small-molecule releasing islands with little off-spot adhesion across the entire array.

FIG. 4.3 illustrates one column in an array similar to that in FIG. 4.2. This array was seeded with SW480 cells and incubated for 4 days. At 80 hours post seeding, the array was pulsed with BrdU for 16 hours and later stained for BrdU incorporation (green/middle column), indicating proliferating cells, and nuclear counter-stain (blue/left-hand column). This figure displays the spots separated by fluorescent channel and a final merged image (right-hand column).

FIG. 4.4 illustrates a release profile from arrays printed with 20% (w/w) coumarin-loaded EVA. The methods were similar to those from FIG. 2.3 with exception of the over-spotted samples illustrated by the green curve (triangles). The red curve (squares) represents arrays printed with single spots of coumarin-loaded EVA, while the green curve represents an extra layer of polymer over-spotted to delay release of the loaded factor.

Example 4

The following figures (FIGS. 5.1 to 5.4) are micrographs taken from drug-eluting cellular microarrays, manufactured as described herein. The images are taken from individual cellular islands from the same array under various drug-loading conditions over a period of three days. HCT116 cells are nuclear stained with Hoechst for easy visibility. All polymer formulations have 5% ELVAX in cyclohexanol (w/w) loaded with 8.5% water phase (loaded with drug) and 8.5% polyvinyl alcohol (to form a stable emulsion). The water phase for this experiment was loaded with azide at various concentrations in addition to a control with no drug loaded. Azide is a useful probe reagent, mutagen, and preservative. Azide inhibits cytochrome oxidase by binding irreversibly to the heme cofactor in a process similar to the action of carbon monoxide. As such, it is expected to induce necrosis in cells at physiologically relevant doses. Our array demonstrates a dose-dependent response to azide as shown in FIGS. 5.1 to 5.4. In the absence of azide (Blank ELVAX), the attached cells appear viable after 68 hour incubation. However, in the presence of azide, cell death is evidenced by the decrease in cell density, which is intensified at the higher concentrations.

Example 5

Colon Cancer Stem Cell and Combinatorial Drug Interaction Screening Using Drug-Eluting Microarrays Modern cancer treatments seek to simultaneously target multiple critical pathways with combinations of chemotherapeutic drugs[1-5]. Intratumor heterogeneity gives rise to varying sensitivity among patients to different classes of chemotherapeutics making it difficult to predict the success of various combination treatments from one patient to the next[1]. This heterogeneity is attributed to a rare population of cancer stem cells (CSCs). Testing possibly new therapies targeted for these CSC's is complicated by the limitation of having very few available cells on which to test drug combinations[6,7]. The present example sought to resolve this challenge with the fabrication of a miniaturized microarray platform to which a minimal quantity of cells can adhere and be exposed to unique treatment conditions. Using this method, colorectal cancer stem-like cells (CCSCs) isolated from two different patients exhibited unique responses to drug combinations when cultured on the microarray, highlighting its potential utility as a prognostic tool for identifying effective, personalized chemotherapeutic regimens.

This platform includes hundreds of drug-loaded polymer islands acting as drug depots that are surrounded by a non-fouling background, thus creating isolated culture environments capable of screening a large number of unique drug combinations on small numbers of cells. The embodiment of the array can screen up to 4,845 unique conditions in the footprint of a standard microtiter plate. Statistically significant results can be obtained by testing approximately one-eighth the amount of cells as a typical 96 well plate experiment. Moreover, the readout of the device is obtained using fluorescence microscopy, allowing for easy translation to laboratory settings. Whereas state-of-the-art industrial pharmaceutical capabilities can surpass this reduction in cell requirements, such facilities are typically unavailable for use by clinicians or core pathology labs. This small, easily manufactured device can be utilized to screen libraries of small molecules on rare cells, establishing a new class of microarray, the drug-eluting cellular microarray.

Materials and Methods:
Polymer Formulation

Poly(ethylene-co-vinyl acetate) (EVA) (Sigma) (40% vinyl acetate by weight) was first washed to remove butyl-hydroxytoluene (BHT) according to a protocol adapted from Langer et al.[29] (reference 29 is hereby incorporated by reference herein). Briefly, polymer pellets were washed ten times each, first in water and then in ethanol at 37° C. with stirring. After each successive wash, the absorbance of the ethanol was analyzed spectrophotometrically at 230 nm to quantify the relative level of BHT until its absorbance was less than twenty times the original reading. Following washing, pellets were dried in a desiccator at room temperature. Polymer pellets were then dissolved in cyclohexanol (Acros, Morris Plains, N.J.) at a 5% w/w concentration.

To embed molecules into the polymer matrix, they were first dissolved in an appropriate solvent, depending on their respective hydrophobicity. A stock solution of azide (99%, Acros), a hydrophilic molecule, was dissolved in $dH_2O$ whereas Nutlin-3a (EMD Chemicals, Gibbstown, N.J.) and camptothecin (Sigma), both hydrophobic molecules, were dissolved in DMSO. Dissolved drugs were then added to 5% EVA at a 1:10 ratio of solvent:EVA. Prior to printing, polymer mixtures were vortexed for 30 s and then homogenized for 1 min before being loaded onto the source plate of the robotic mini-arrayer.

Array Fabrication

Glass coverslips were cleaned in an oxygen plasma etcher (Terra Universal, Fullerton, Calif.). Arrays of isolated spots of (3-Aminopropyl) trimethoxysilane (NH2-terminated silane) (Sigma-Aldrich, St. Louis, Mo.) were robotically printed on clean coverslips using a Calligrapher Miniarrayer printer (Bio-Rad, Hercules, Calif.) with 1500 μm center to center distances and a pin diameter of 400 μm. The silane printed coverslips were then coated with 175 Å of titanium (Ti; 99.995% pure) and 225 Å of gold (Au; 99.999% pure)

Figure 6B:
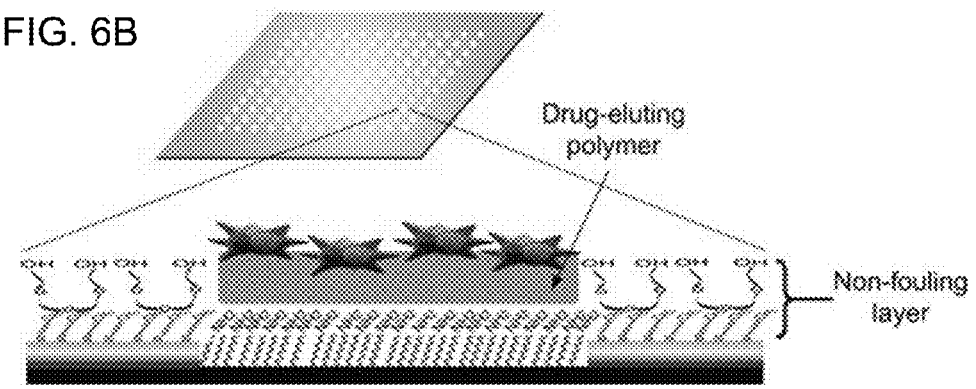

(Williams Advanced Materials, Buffalo, N.Y.). Following coating, gold-coated arrays were sonicated to remove gold from the amine spots, exposing NH2-terminated silane islands. The coverslips were incubated with 0.1 M, methyl-terminated alkanethiol ($CH_3(CH_2)_{11}SH$) (Sigma) for 30 min. Substrates were incubated in 10% Pluronic® F-127 (BASF Corporation, USA) for 3 h and 1% heat-denatured BSA for 30 min to create a non-fouling surface around the adhesive amine islands. Three layers of the drug-loaded ethylene vinyl acetate (EVA) polymers were printed over the amine islands and placed in a desiccator between each successive layer. Poly-d-lysine (0.1%) was over-spotted onto the EVA films to promote cell attachment. (The EVA film was fabricated using water-oil emulsion to promote uniform film thickness during drying, and had a mottled appearance) The arrays were placed in 35 mm petri dishes containing PBS with 2% penicillin and 2% streptomycin for 15 minutes to rehydrate the non-fouling PEG background and as a non-caustic sterilization step. Schematic diagrams of the arrays are illustrated in FIGS. 6A and 6B.

Drug Release and Loading Efficiency

To test the effect of over-spotting on release of drugs, 5% EVA in cyclohexanol was loaded with 20% (w/w) 7-Diethylamino-4-methycoumarin (Acros Organics, Morris Plains, N.J.) and printed onto glass coverslips in an arrayed fashion as described above. Following printing, arrays were placed in 35 mm petri dishes with 3 ml PBS, and 20 µl samples were taken at defined intervals and analyzed on a Wallac 1420 Multilabel Counter (PerkinElmer, Waltham, Mass.). For over-spotted samples, unloaded EVA was immediately printed over the dye-loaded islands before being incubated in PBS. Sampling and analysis thereafter were identical.

To determine the loading efficiency of factors, polymer formulations were made as described above. Films derived from 100 µl EVA loaded with factors were then made on glass coverslips and allowed to dry overnight under vacuum. Films were removed from the glass substrates and weighed. Films were washed briefly with PBS before being placed in 1 ml toluene to dissolve the polymer. Samples were then analyzed using a Nanodrop-ND-1000 spectrophotometer. Standard curves were generated for each factor, and loading efficiency was calculated as the percent of drug embedded in the polymer compared to the theoretical drug concentration.

For drug release studies, polymer formulations were again made as described above. Glass coverslips were weighed prior to printing. Arrays consisting of 900 drug-loaded polymer islands were manufactured and allowed to dry overnight. Samples were weighed and placed in 3 ml of PBS containing 0.1% Tween-80 at 37° C. with gentle agitation. Samples were taken at the specified times and analyzed.

Human Subjects

Tissues from colon cancer patients were retrieved under pathologic supervision with Institutional Review Board approvals at the University of Michigan and the University of Florida as previously described[32] (reference 32 is hereby incorporated by reference herein with respect to obtaining tissue samples from colon cancer patients).

Cell Lines and Seeding

HCT116 (p53+/+, ATCC, Manassas, Va.) human colon cancer cells were maintained in McCoy's 5a Medium supplemented with 10% fetal bovine serum (Thermo Scientific, Waltham, Mass.), 1% penicillin G and 1% streptomycin (Thermo Scientific). The cells were cultured at 37° C. in a humidified incubator containing 5% $CO_2$. Following microarray fabrication, 100,000 HCT116 cells were seeded over each array in 3 ml serum-free media and allowed to incubate on a rocking plate at room temperature until cell attachment to the EVA islands occurred, with minimal attachment to background, typically 10-15 min. Microarrays were gently washed in PBS, placed in a 35 mm petri dish with complete media, and placed in an incubator for 24-72 h.

$ALDH^{high}$ spheres were generated from tumor cells obtained from patients with colon cancer. Isolated cells were cultured in serum-free media as previously described[14] (reference 14 is hereby incorporated by reference herein with respect to methods for culturing cells in serum-free media). Using these cultures, adherent cell growth was established with 0.1% gelatin (Millipore) coatings on tissue culture plates (TPP, Switzerland) and the cells were serially propagated. For CA1 and CA2 cells, 25,000 cells were tested per array. Cells were seeded in PBS with 0.1% gelatin and treated identically to the microarrays with HCT116.

For p53 mutational analysis, genomic DNA was isolated using a DNeasy Tissue kit (Qiagen GmbH, Hilden, Germany); exons 4-9 were amplified with a Taq polymerase Master Mix (Promega, Madison, Wis.) using a Touchdown PCR program (45 cycles; 60° C. to 50° C.; 0.5° C. decrease per cycle) and previously described primers[33] (reference 33 is hereby incorporated herein with respect to the primers). The resulting PCR products were fractionated by agarose gel electrophoresis; excised and isolated using a QIAquick extraction kit (Qiagen GmbH, Hilden, Germany) and sequenced using an ABI 3130xl Genetic Analyzer (Applied Biosystems, Carlsbad, Calif.). Sequences were analyzed using Sequencher v. 5.0 (Gene Codes, Ann Arbor, Mich.).

To establish microarray fidelity, microarrays were manufactured as described above. HCT116 cells were then seeded over microarrays and incubated for 24 or 72 h. Microarrays were fixed in 4% paraformaldehyde and stained with Hoechst 34580 dye.

Staining and Image Analysis

Camptothecin-loaded microarrays were stained with Annexin V (BD Pharminigen), fixed in 4% paraformaldehyde, and placed in PBS with Hoechst dye 34580 (Invitrogen, USA) for 30 min. Azide-loaded microarrays were fixed with 4% paraformaldehyde and incubated with PBS containing Hoechst 34580 dye. Finally, nutlin-3a-loaded microarrays were fixed with 4% paraformaldehyde, stained with BrdU (BD Bioscience, San Jose, Calif.), and incubated in PBS containing Hoechst 34580 dye. All arrays were mounted with Fluoro-Gel (Electron Microscope Sciences, Hatfield, Pa.) and imaged using an Axiovert 200M microscope (Carl Zeiss, Oberkochen, Germany). Analysis was performed with Axiovision (Carl Zeiss, Oberkochen, Germany) by quantifying, in each drug-eluting island, the area of fluorescence and reported as relative fluorescence intensity (RFI).

Crosstalk

To evaluate the potential influence of neighbouring drug-eluting islands on the array, multiple arrays were printed in randomized configurations. Data were then analysed using student's t-test to see if pairs with significant crosstalk existed between the same groups (i.e., the outcome changed when the pairs were arranged differently on the array).

Calculating Comparison to Microtiter Plates

Dimensions for a typical microtiter plate were obtained from Corning®. The length×width is 127.8 mm×85.6 mm. Based on island spacing of 1.5 mm, 85 islands (i.e., (127.8)/(1.5)) can fit along the length axis, and 57 (i.e., (85.6)/(1.5)) islands can fit along the width of a traditional plate. Thus (85×57) yields 4845 total islands that fit within the footprint of a standard microtiter plate. For calculating the comparison between the amount of cells required for a traditional screen using a 96 well plate 10,000 cells per well was assumed as a typical seeding density. Performing experiments in triplicate with 16 unique drug combinations therefore requires 480,000 cells total (i.e. (10,000)*(16)*(3)).

Statistical Analyses

Statistical analyses were performed using either a one-way ANOVA or a two-way ANOVA, using Systat (Version 12, Systat Software, Inc., San Jose, Calif.). Post-hoc pairwise comparisons were made using Tukey's Honestly-Significant-Difference, with p≤0.05 being significant. Curve-fitting of drug-release and dose-response curves were performed using SigmaPlot (Version 10, Systat Software, Inc., San Jose, Calif.).

Proliferation values were normalized to control (0 µM drug). Values for concentration-response curves were transformed to non-proliferation by subtracting the normalized value from 100%. Curve fitting analysis was performed to obtain $E_{max}$ and $D_{50}$ values using the equation $E=E_0+(E_{max} \times D)/(D+D_{50})$ where E is the effect (either non-proliferation or apoptosis), $E_0$ is the initial value, $E_{max}$ is the maximum effect, D is the dose, and $D_{50}$ is the dose at which a 50% maximum effect ($E_{max}$) is observed[34]. Drug sensitivity values were obtained by taking the inverse of the $D_{50}$ and multiplying by 100. Those values marked with "#" indicate that the $r^2$ value of the curve-fit was below 0.65. N/A values are present where negative parameters were obtained.

Results & Discussion

The present example describes development of a drug-eluting cellular microarray to screen libraries of small molecules for their effects on populations of rare cells. Arrays with PEG-based non-fouling backgrounds and amine-terminated silane adhesion islands were manufactured as reported[20] (Reference 20 is hereby incorporated by reference herein with respect to manufacturing of the described PEG-based arrays. (FIG. 6a). Micropatterning of NH2-terminated silane onto the glass substrate provided 400 µm diameter islands. PEG was back-filled around the silane islands to resist cell attachment off-spot (FIG. 6b). These silane islands were then over-spotted with oil/water emulsions of ethylene vinyl acetate (EVA) loaded with drugs of interest or unloaded (control). EVA is a biocompatible polymer commonly used in drug delivery applications, and when formulated as an oil/water emulsion both hydrophilic and hydrophobic molecules can be loaded[30, 31]. Dry polymer films were over-spotted with poly-d-lysine to facilitate cell adhesion.

Figure 6C:
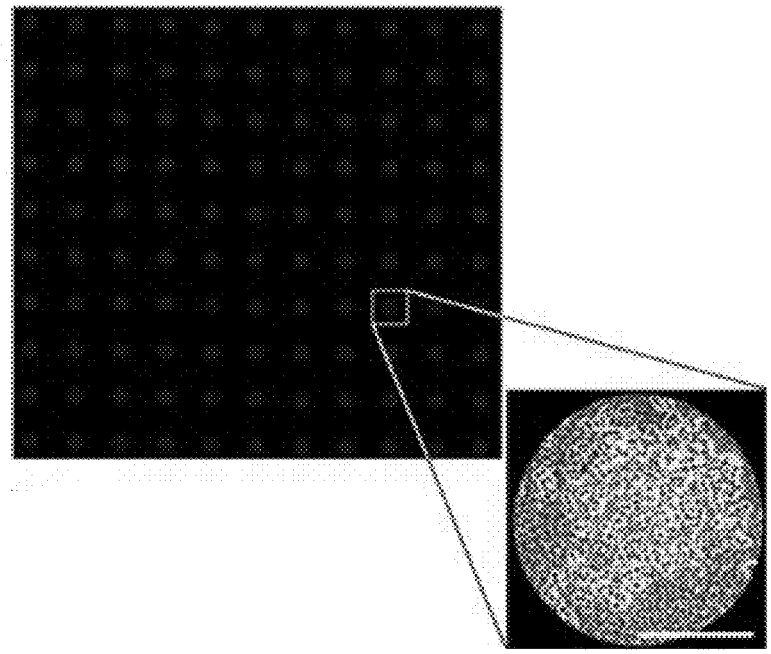

Site-specific attachment of cells to polymer islands with minimal cell adhesion to the background was achieved (FIG. 6c). Fidelity of fabrication and cell attachment was quantified at 24 h incubation using the following criteria (results in parentheses): (1) lysine printing misalignment with polymer islands (<1.3%); (2) proportion of islands with adherent cells (>95%); (3) islands with <65% cell coverage (<11%); (4) proportion of cells on islands (vs. background) (>94%).

Figure 8A:
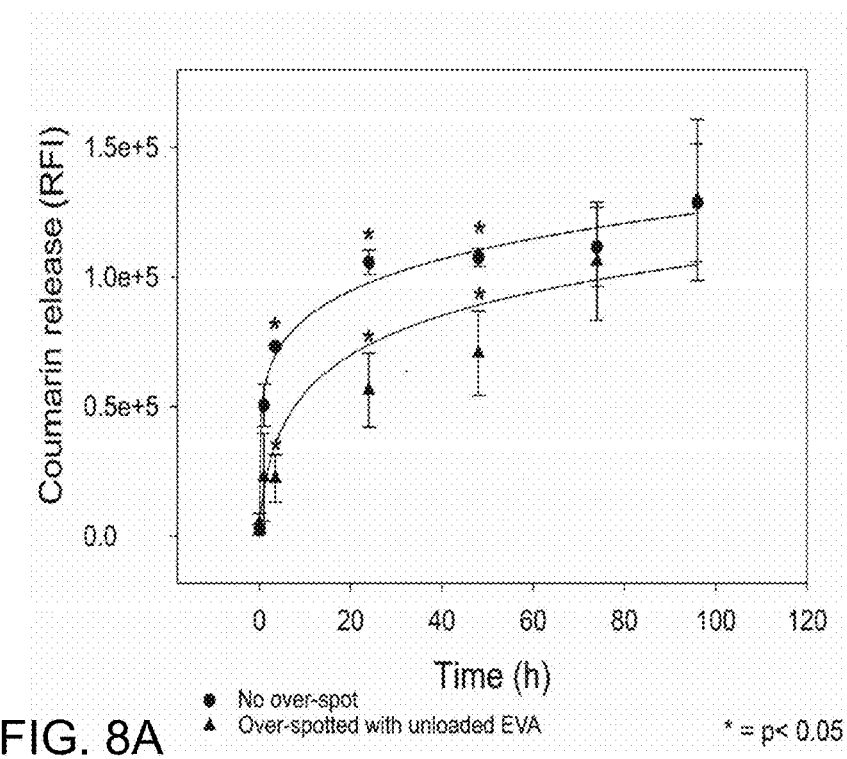
FIG. 8A is a graph illustrating the release kinetics of coumarin-loaded EVA films and showing that overspotting of unloaded EVA over coumarin-loaded EVA mitigates bolus release. (*: $p<0.05$). The bar graph in FIG. 8B illustrates cell counts of HCT116 on azide loaded film after attachment. (Microarrays were fixed with 4% paraformaldehyde and stained with Hoechst 34580 nuclear dye 1 h after seeding to quantify initial cell density. No statistical difference was found by ANOVA (p=0.490)).
Figure 8B:
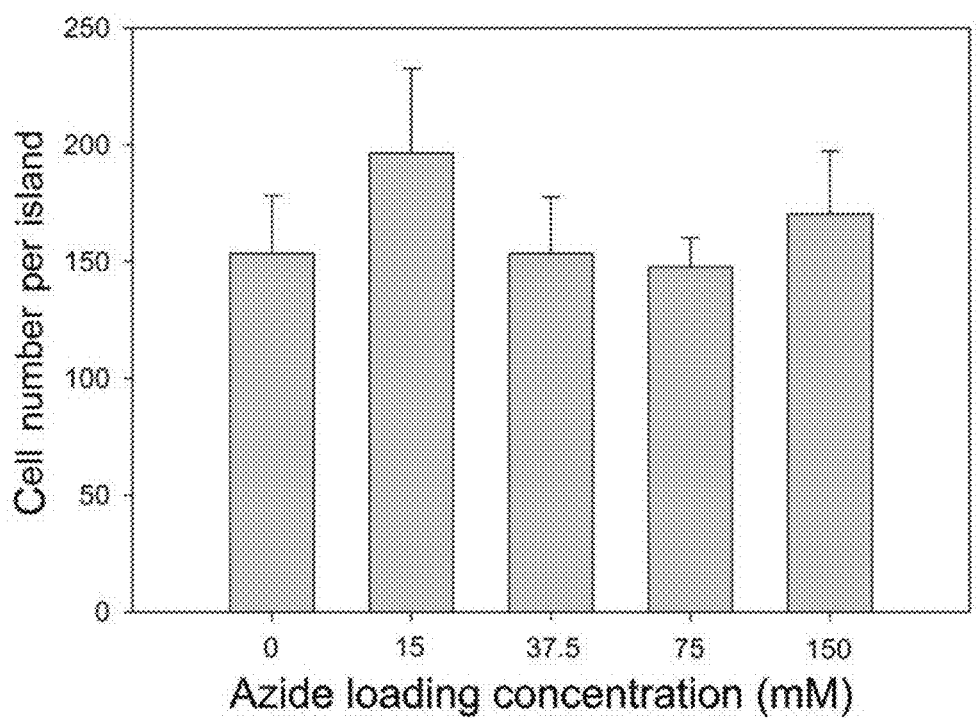

Loading efficiency of small molecules from EVA films on the microarrays was quantified (Table 1). Release kinetics from microarrayed drug-eluting EVA films demonstrated an initial burst during the first 24 h followed by a steady rate of release over four days (FIGS. 7A and 7E). Drug release can be delayed by over-spotting unloaded EVA films onto drug-loaded films, creating a diffusion barrier (FIG. 8A). Cell number per island at 1 h was unaffected by drug loading concentration (FIG. 8B).

TABLE 1

Loading efficiencies of small molecules in microarrayed EVA films.

| Compound | Loading efficiency (%) |
|---|---|
| Azide | 73 +/− 8 |
| Camptothecin | 92 +/− 3 |
| Nutlin-3a | 81 +/− 7 |

Figure 9A:
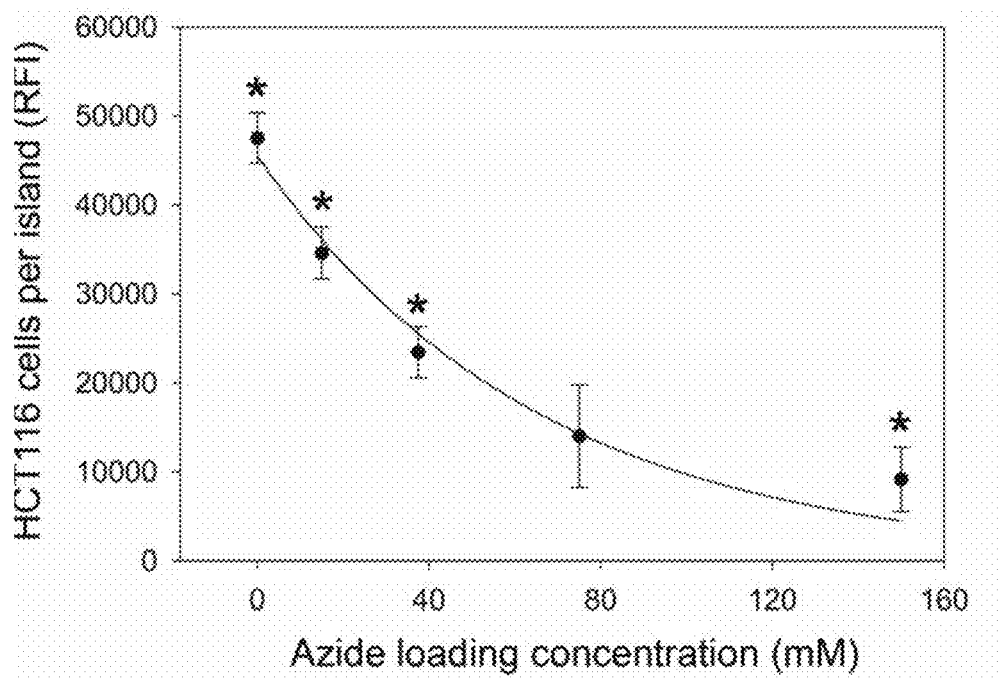
FIGS. 9A-9B are graphs illustrating that HCT116 cell numbers exhibit dose dependent responses to drug loading concentration. Cell numbers decreased with increasing loading concentrations of azide after 24 h (FIG. 9A) and nutlin-3a after 72 h (FIG. 9B). (*: $p<0.05$ compared to all other concentrations).
Figure 9B:
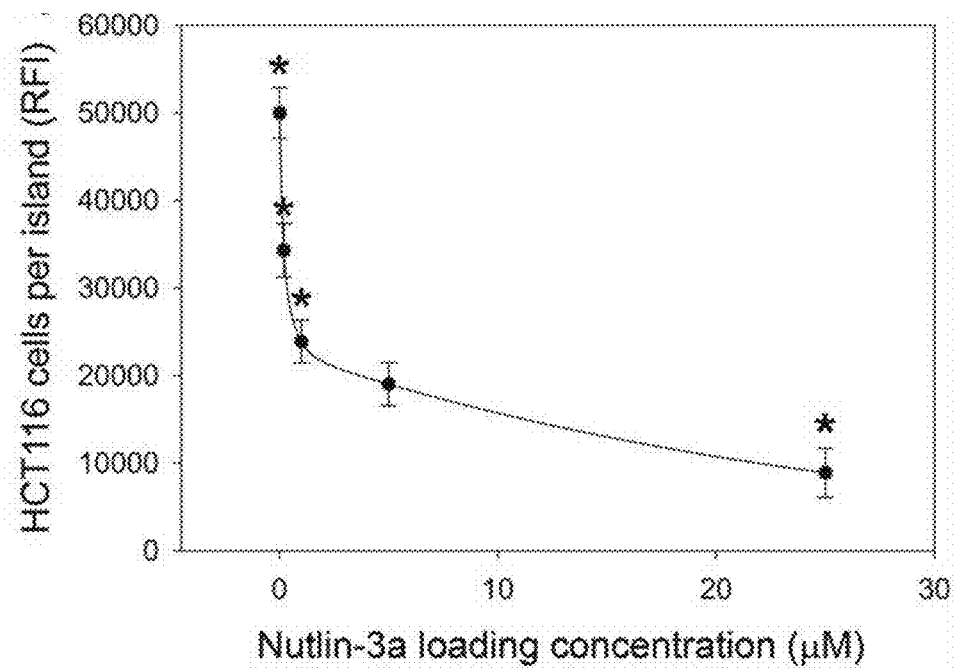

Feasibility of eliciting dose-dependent responses to hydrophilic drugs was demonstrated (FIG. 9A). Having thus demonstrated feasibility, two classes of clinically relevant drugs were investigated. Nutlin-3a is a hydrophobic drug that inhibits human double minute 2 (HDM2) and is being investigated clinically in combination with numerous therapeutic agents[21]. Nutlin-3a binding to HDM2 disrupts turn-over of p53, increasing p53 protein levels and inducing cells to enter into either a state of cell cycle arrest, or apoptosis at higher concentrations[22, 23]. HCT116 cells were cultured on nutlin-3a loaded microarrays for 24 h and proliferation was quantified. With increasing concentrations of nutlin-3a, the ratio of non-proliferating cells expanded (FIGS. 7B-7D). Correspondingly, cell numbers were diminished following 72 h incubation (FIG. 9B). Hence, the HCT116 cell line evidenced dose-dependent cell cycle arrest when cultured on nutlin-3a loaded microarrays. Camptothecin, a hydrophobic topoisomerase inhibitor that induces apoptosis is also of interest as various analogues are used in chemotherapy[24, 25]. As expected, the proportion of HCT116 cells undergoing apoptosis was greater with increasing concentrations of camptothecin after 72 h incubation on the microarray (FIGS. 7F-H).

Seminal cell-based microarray studies previously demonstrated that experimental design can control for undesirable interactions between islands through island spacing, randomized configurations and robust statistical analysis[26]. Prior work on a different microarray configuration indicated 1.5 mm spacing between islands was sufficient to isolate cell populations from agents released from neighboring islands[27]. To corroborate with the setup of this example, and determine whether paracrine signaling or leaching of drugs from adjacent polymer islands occurred using this 1.5 mm island spacing, camptothecin loaded arrays were analyzed in a variety of configurations (FIGS. 7I and 7J). No significant differences were noted between the configurations, indicating the negligible interaction with cells or drugs from neighbouring islands (FIG. 7K).

Figure 10A:
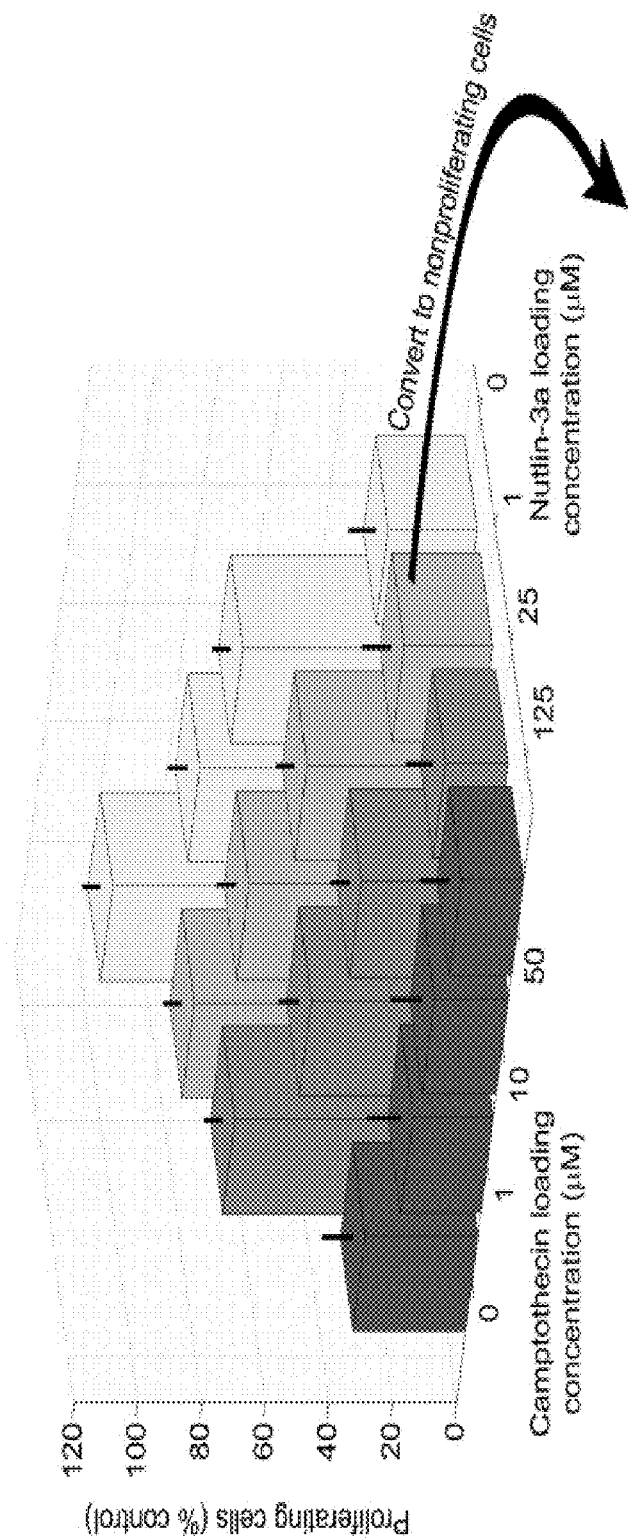
Figures 10F, 10G, 10H, 10I:
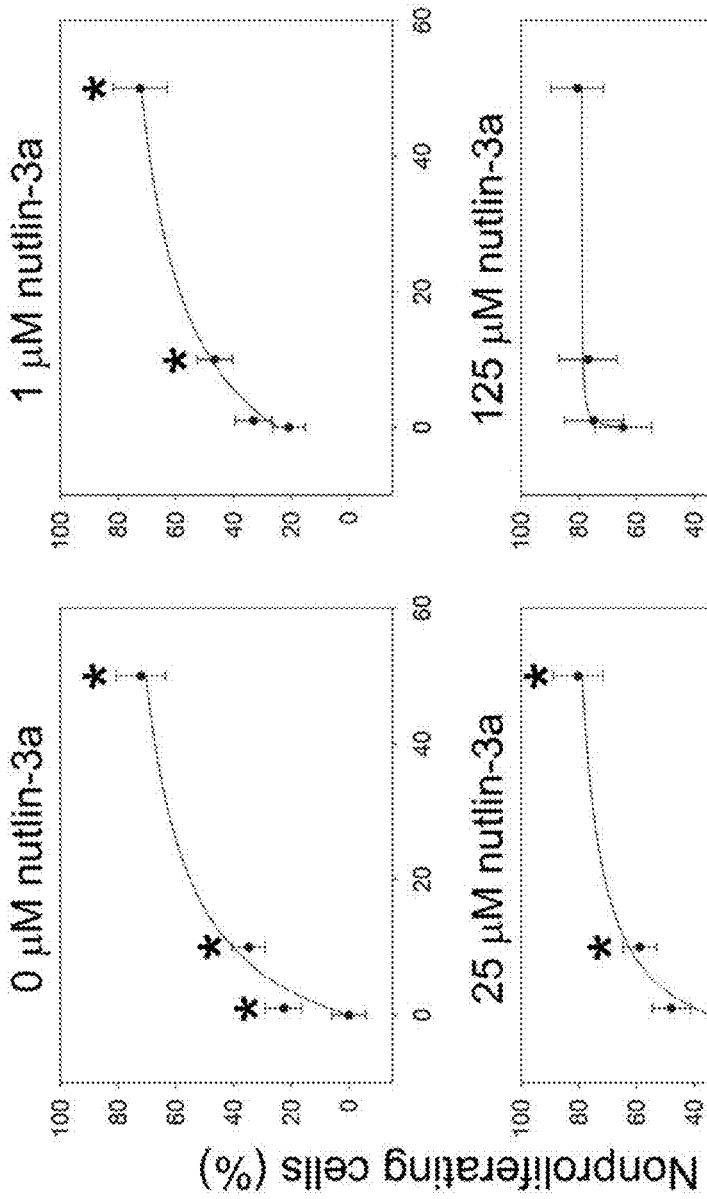
Figure 11A:
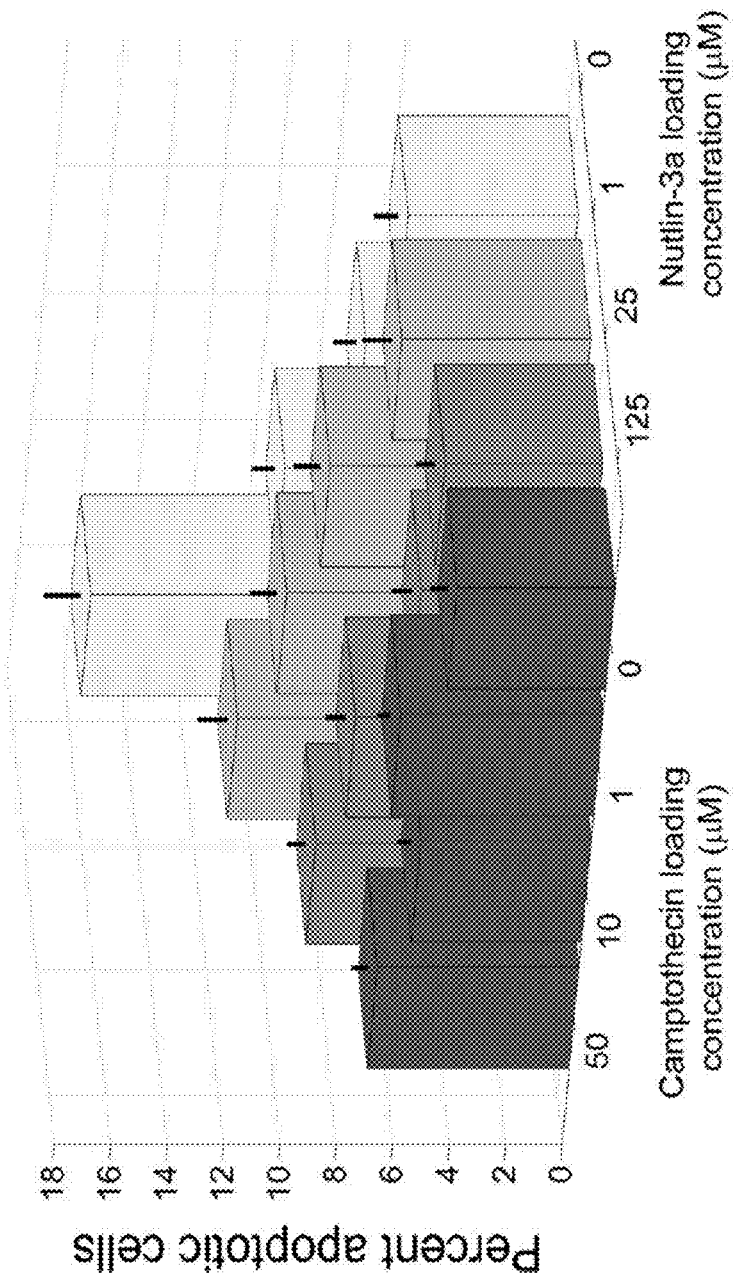

Chemotherapy for colorectal cancer is often a combination of two drugs. Dual-drug microarrays were developed to investigate possible interaction effects of nutlin-3a and camptothecin on the HCT116 cell line. Ranges of loading concentrations for the two drugs were combinatorially encapsulated and spotted in randomized microarray configurations (FIG. 7L). Results demonstrate feasibility of the drug-eluting microarray approach to identify combined effects of drugs on proliferation (FIGS. 10A-10I, Table 2), and apoptosis (FIGS. 11A-11I, Table 3) using the HCT116 cell line. Following 24 h incubation with both nutlin-3a and camptothecin, proliferation of HCT116 cells significantly decreased (FIG. 10A). A significant primary effect on proliferation relative to nutlin-3a, {F(3,619)=18.253, p<0.01}, and camptothecin, {F(3,619)=25.056, p<0.01} was revealed by two-way ANOVA. Additionally, a sub-additive effect was observed from combination treatments. Camptothecin increased sensitivity to nutlin-3a and vice versa (FIGS. 10B-I). By contrast, the Emax values were unaffected by combination drug treatments, as values obtained from single drug regimens were already at maximum levels. This indicates that in HCT116 cells, a maximum plateau effect is present when evaluating proliferation in the presence of nutlin-3a and camptothecin, though significantly lower concentrations are able to obtain a given effect when these drugs are used in concert. Nutlin-3a showed no effect on the proportion of HCT116 cells that underwent apoptosis when administered alone (6.0% for 0 μM vs 5.6% for 125 μM, p>0.05) (FIGS. 11A, 11B). A greater percentage of cells underwent apoptosis after exposure to camptothecin. (FIG. 11F). Increasing the nutlin-3a concentration conferred protection from the apoptotic response to camptothecin, particularly evident at higher fixed concentrations of camptothecin (FIGS. 11C-11E), and addition of nutlin-3a attenuated the apoptotic response to camptothecin[35, 36], resulting in a 65% decrease in the $E_{max}$ of the camptothecin concentration response curve in the presence of 125 μM nutlin-3a compared to 0 μM nutlin-3a (FIGS. 11F-11I).

Figure 12A:
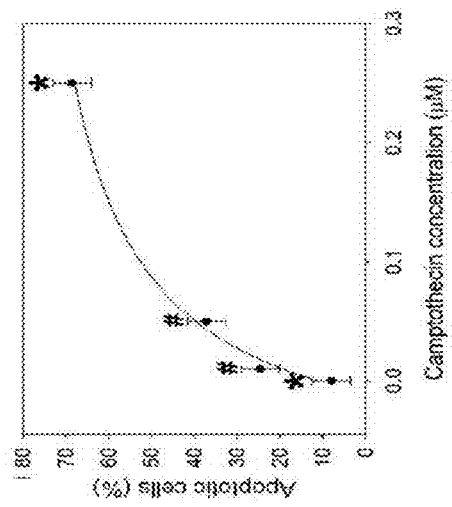
FIGS. 12A-12D are a series of graphs illustrating apoptosis and proliferation dose-response curves from HCT116 cells incubated with soluble drugs.
Figure 12B:
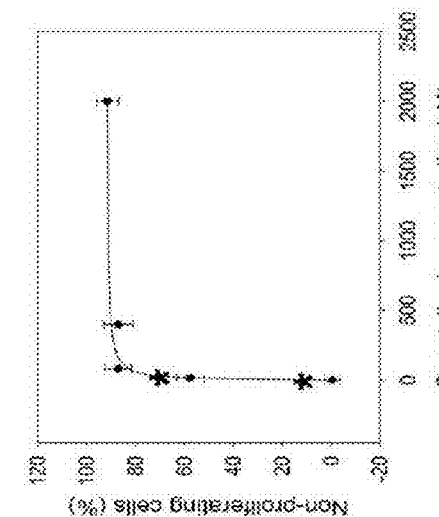
Figure 12C:
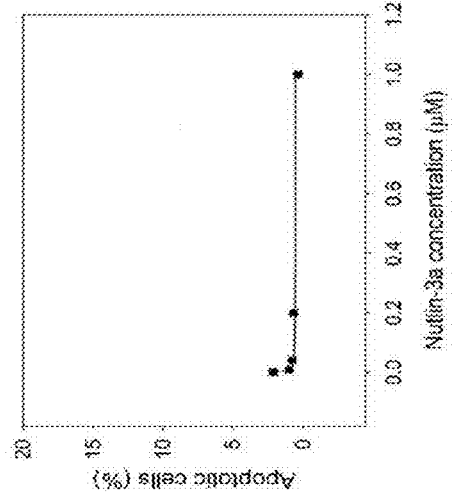
Figure 12D:
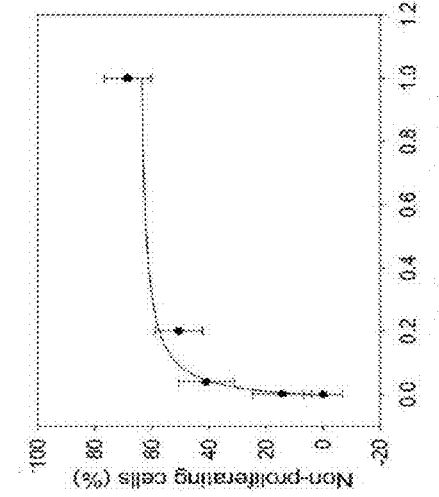

Hyperbolic curve fits were generated for the dose responses from a first drug in the presence of a fixed amount of a second drug for each combination (Tables 2 and 3, below). The curves were modeled using the following equation $$E = E_o + E_{max} \cdot C/(C+D50)$$

where $E_{max}$ is the maximum biological response obtainable, $(1/D_{50})$ is the sensitivity (where an increasing value indicates a lower necessary dose to approach $E_{max}$), and C is the concentration.

a dose-dependent effect on reducing proliferation of HCT116 cells (FIGS. 12C-12D).

CCSCs have recently been linked to tumor initiation, potentiation, and as the genesis for metastatic deposits[11]. The cancer stem cell hypothesis states that these rare cells, constituting <10% of the tumor mass, are responsible for both the heterogeneity and the hierarchy within the tumor[7, 10]. As these cells are challenging to isolate and target therapeutically, they were selected as targets to determine the feasibility of the microarray to delineate the potency of pathway-specific chemotherapeutic agents. CCSCs were thus isolated and enriched for aldehyde dehydrogenase (ALDH) from patients with colon cancer and propagated as spheroid cultures as recently described[14, 15, 17] (References 14, 15, and 17 are hereby incorporated by reference herein with respect to the propagation of CCSCs as spheroid cultures). Two such patient-derived populations of CCSCs, labeled herein as CA1 and CA2, were investigated. In contrast to HCT116 cells, which express wild type p53, both CA1 and CA2 have a single base pair transition substitution at amino acid 273 of the DNA binding domain (arginine to histidine). For compatibility with drug-eluting microarrays, adherent cell growth was established and serially propagated. Phenotypes were compared to those maintained as spheroid cultures with regards to expression of ALDH and mucin 2 (MUC2, which delineates differentiation along the goblet cell lineage). While ALDH expression was maintained in CA1 cells, in CA2 cells, the proportion of cells expressing ALDH declined from 75% in cells cultured in

TABLE 2

$E_{max}$ and $D_{50}$ values generated from combinatorial microarrays of HCT116 cells.
HCT116 Proliferation

| | | Hyperbolic Fit Parameters of Nutlin Dose Response Upon Addition of Camptothecin | | | | | Hyperbolic Fit Parameters of Camptothecin Dose Response Upon Addition of Nutlin | | |
|---|---|---|---|---|---|---|---|---|---|
| $2^{nd}$ Drug | Conc (μM) | $E_{max}$ | $\frac{1}{D50} \times 100$ | Source Data | $2^{nd}$ Drug | Conc (μM) | $E_{max}$ | $\frac{1}{D50} \times 100$ | Source Data |
| CPT | 0 | 108 +/− 110 | 3.00 +/− 0.49* | Sup FIG. 4b | NUT | 0 | 86.4 +/− 39 | 4.83 +/− 0.54* | Sup FIG. 4f |
| | 1 | 96.1 +/− 25 | 1.78 +/− 1.7 | Sup FIG. 4c | | 1 | 88.8 +/− 20 | 5.65 +/− 5.2 | Sup FIG. 4g |
| | 10 | 86.5 +/− 19 | 2.97 +/− 3.7 | Sup FIG. 4d | | 25 | 86.3 +/− 22 | 12.1 +/− 18 | Sup FIG. 4h |
| | 50 | 81.4 +/− 1.9 | 19.6 +/− 12 | Sup FIG. 4e | | 125 | 79.1 +/− 3.7 | 78.1 +/− 26* | Sup FIG. 4i |

TABLE 3

$E_{max}$ and $D_{50}$ values generated from combinatorial microarrays of HCT116 cells undergoing apoptosis.
HCT116 Apoptosis

| | | Hyperbolic Fit Parameters of Nutlin Dose Response Upon Addition of Camptothecin | | | | | Hyperbolic Fit Parameters of Camptothecin Dose Response Upon Addition of Nutlin | | |
|---|---|---|---|---|---|---|---|---|---|
| $2^{nd}$ Drug | Conc (μM) | $E_{max}$ | $\frac{1}{D50} \times 100$ | Source Data | $2^{nd}$ Drug | Conc (μM) | $E_{max}$ | $\frac{1}{D50} \times 100$ | Source Data |
| CPT | 0 | 95.2 +/− 9.2# | N/A | Sup FIG. 5b | NUT | 0 | 21.6 +/− 3.0* | 2.53 +/− 1.1 | Sup FIG. 5f |
| | 1 | 112 +/− 23# | N/A | Sup FIG. 5c | | 1 | 12.8 +/− 2.5 | 83.3 +/− 76 | Sup FIG. 5g |
| | 10 | 79.3 +/− 9.7 | 2.48 +/− 0.83 | Sup FIG. 5d | | 25 | 9.31 +/− 2.5 | 15.9 +/− 2.8 | Sup FIG. 5h |
| | 50 | 131 +/− 38 | 143 +/− 98 | Sup FIG. 5e | | 125 | 7.46 +/− 2.5* | N/A | Sup FIG. 5i |

Figure 13A:
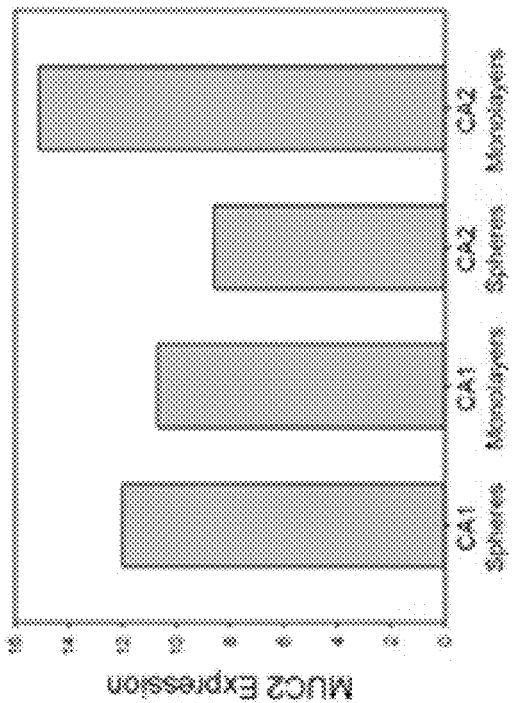
FIGS. 13A-13B are bar graphs illustrating ALDH and MUC2 expression in patient-derived CCSCs.
Figure 13B:
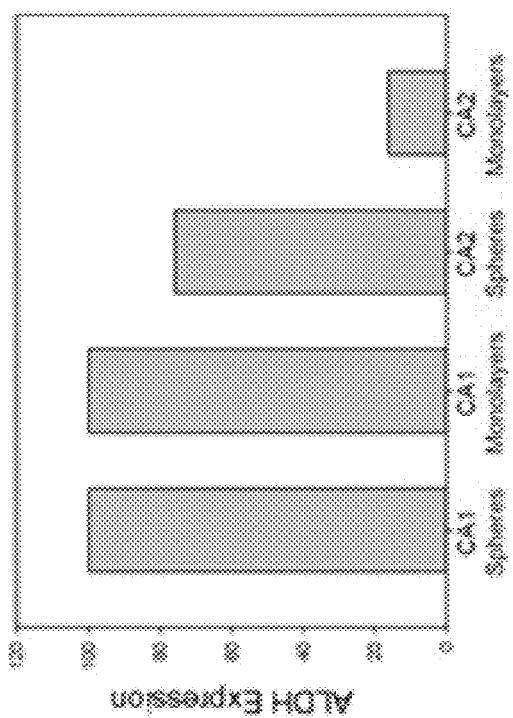

Results were corroborated using soluble drugs in 96-well plates (FIGS. 12A-D). Results showed no effect of nutlin-3a on inducing apoptosis of HCT116 cells (FIG. 12A), similar to results shown on microarray. Camptothecin displayed a dose-dependent effect on inducing apoptosis of HCT116 cells (FIG. 12B). Nutlin-3a and Camptothecin both showed spheroid form to 16% of cells in the adherent form. Correspondingly, MUC2 expression increased from 9% (spheroid) to 15% (adherent) (FIGS. 13A-B).

Figure 14A:
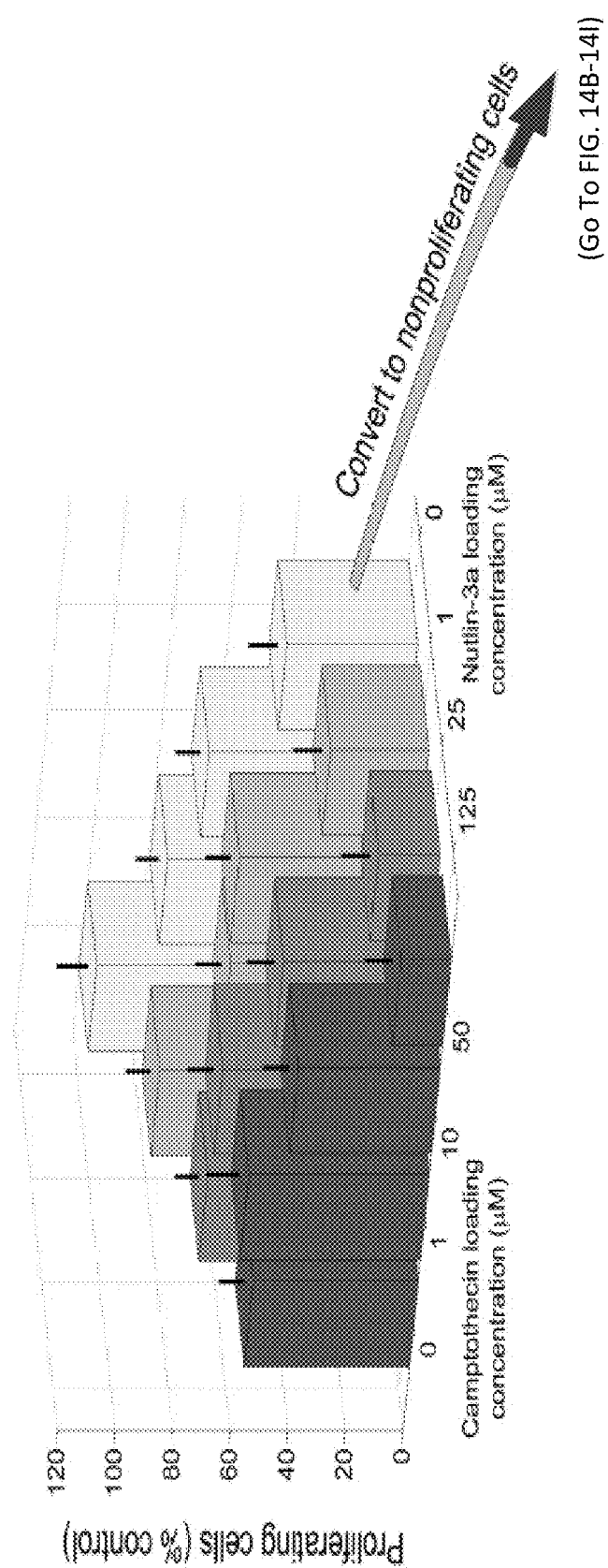
Figures 14B, 14C, 14D, 14E:
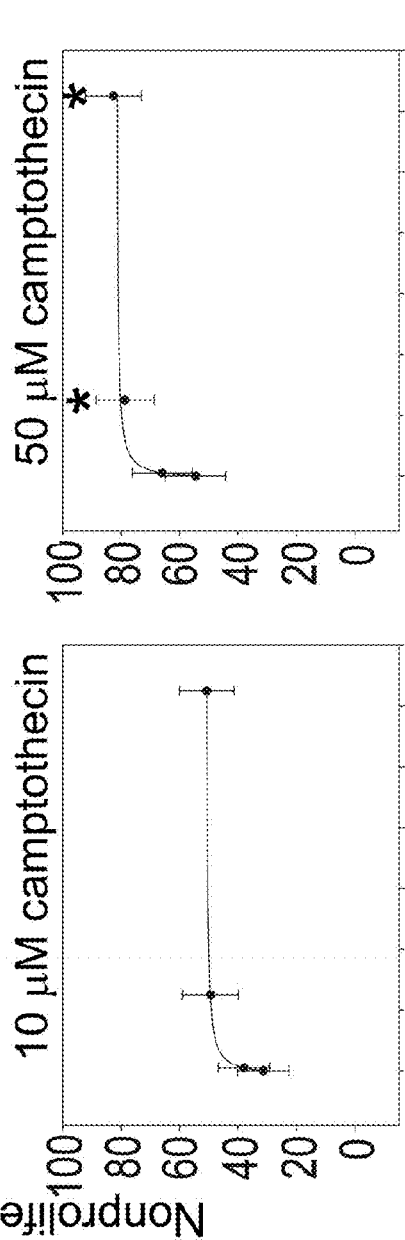
Figure 14J:
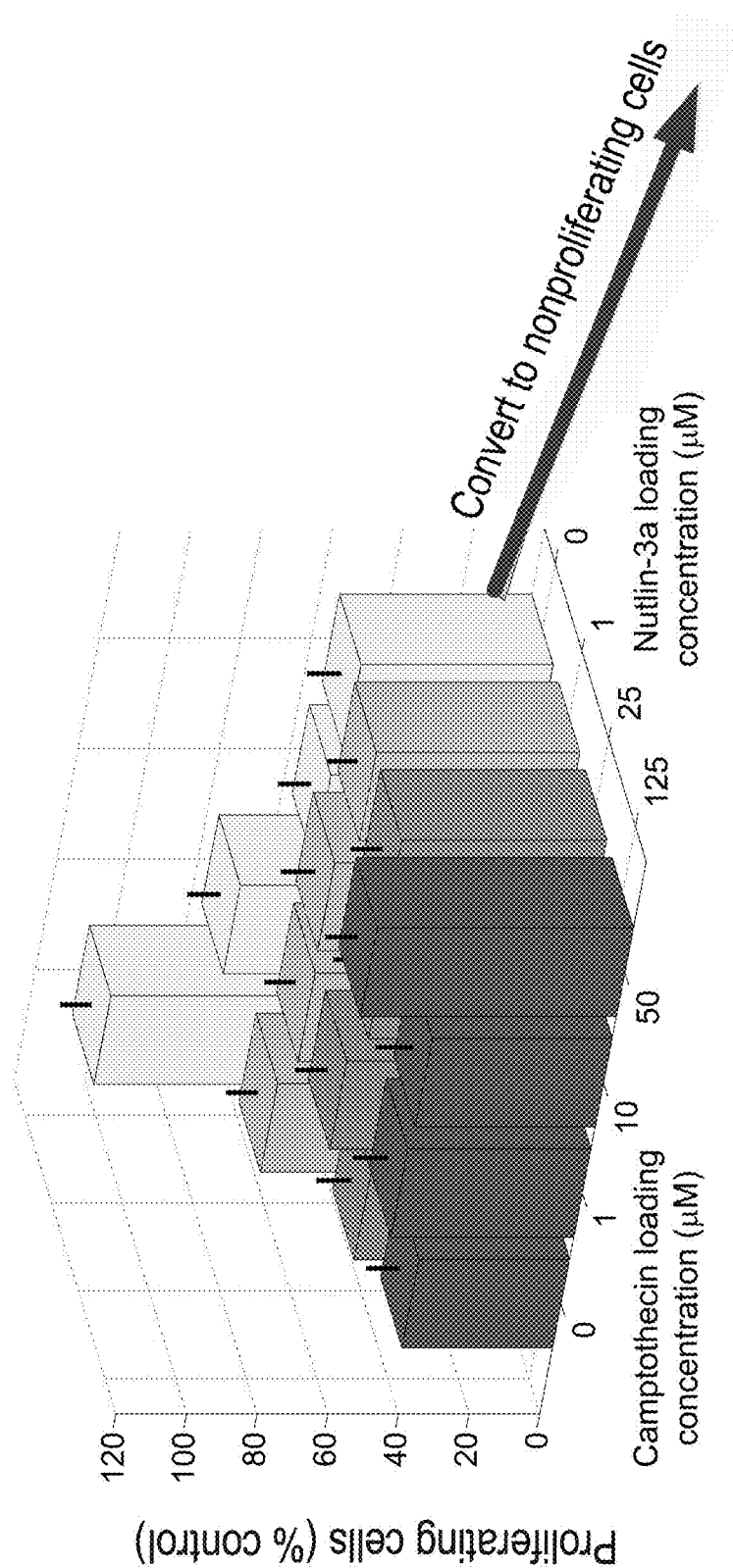
FIG. 14J is another three dimensional graph illustrating proliferation response of CA2 cells on drug-eluting cellular microarrays.
Figure 14K:
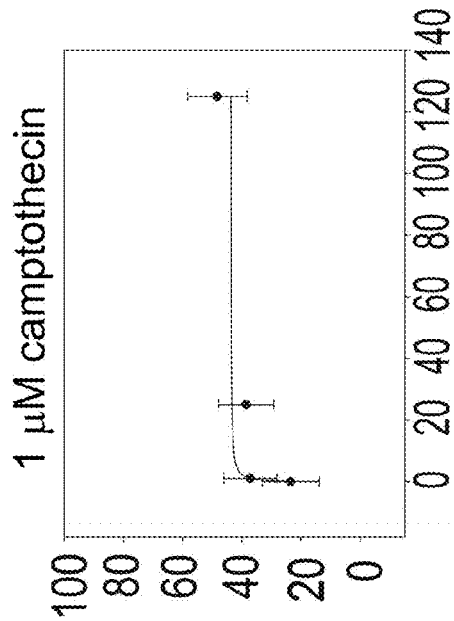
Figure 14L:
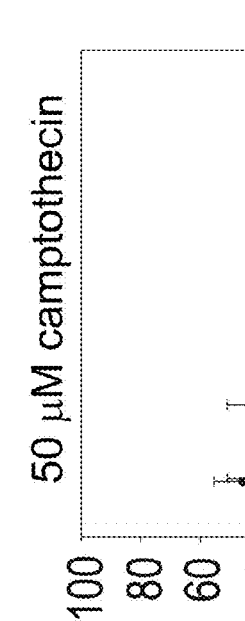
Figure 14M:
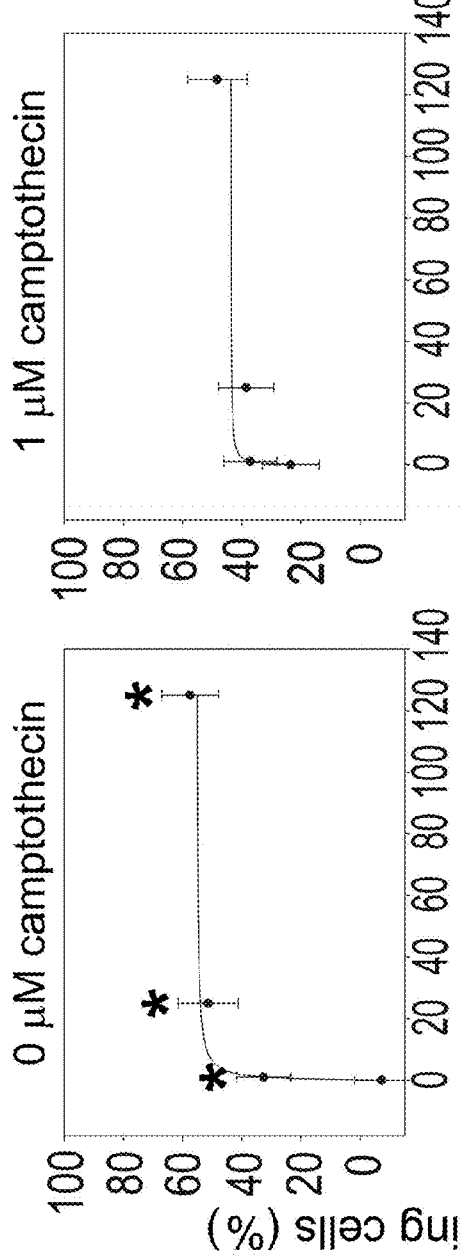
Figure 14N:
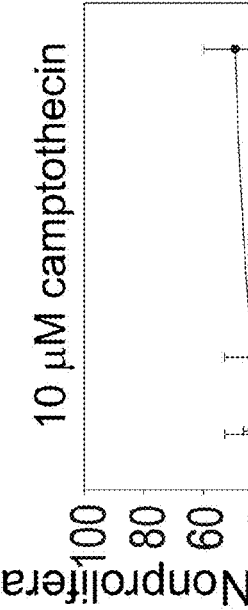

Different trends were observed for CCSCs from each patient when exposed to camptothecin and nutlin-3a combinations on the microarrays (FIGS. 14A and 14J). Cells from both patients exhibited decreasing proliferation with increasing nutlin-3a or camptothecin exposure (FIGS. 14A, 14B, 14F, 14J, 14K, and 14O). For CA1 cells (FIGS. 14B-14I) sub-additive effects were observed from combination treatments. Significant effects on proliferation due to nutlin-3a, {F(3,233)=5.762, p<0.01}, and camptothecin, {F(3,233)=16.884, p<0.01} were found by ANOVA. Trends were evident, indicating increased antiproliferative activity with combination treatments. For CA2 cells (FIGS. 14K-14R), significant primary effect on proliferation due to nutlin-3a was revealed {nutlin-3a, F(3,329)=2.854, p=0.037}, though not to camptothecin {F(3,329)=0.508, p=0.677} by ANOVA. Additionally, an antagonistic effect was observed from combination treatments {F(9,329)=2.382, p=0.013}, where increasing both drugs reversed drug-induced non-proliferation compared to high doses of individual drugs. Negative slopes at high doses indicate an antagonistic interaction (FIGS. 14N, 14R). The concentration response curves indicated significant differences between patients (FIGS. 14B-14I and 14K-14R). To assess these differences, maximum response ($E_{max}$) and drug sensitivity values ($1/D_{50}$) were obtained by hyperbolic fit to the concentration response curves (Tables 4 and 5).

induced increase in p73 expression, which can promote genes required for cell cycle arrest, senescence, and apoptosis as previously shown[28]. Alternatively, the p53 mutation in the CCSCs could be silent.

These results demonstrate that CA1 and CA2 cells differ greatly in their responses to combinations of drugs. Cells from patient CA1 exhibited an improved reduction in proliferation. In particular, introduction of camptothecin significantly increased the anti-proliferative activity of nutlin-3a in this patient's CCSCs. In contrast, responses from CA2 cells were less pronounced to drug combinations, with treatments interacting antagonistically. CA2 cells exhibited significant responses to either nutlin-3a or camptothecin treatment alone, but combination treatments muted anti-proliferative effects. Therefore, in contrast to CA1, CA2 cells may respond to topoisomerase I inhibitors or p53 activating agents alone or possibly with other classes of agents, to achieve an increased reduction in proliferation.

The present example demonstrates creation of a novel platform capable of performing chemosensitivity screens on patient-derived CCSCs using limited cell numbers. The results presented here (i) indicate that there can be consid-

TABLE 4

$E_{max}$ and $D_{50}$ values generated from combinatorial microarrays of CA1 CCSCs.
CA1

| | | Hyperbolic Fit Parameters of Nutlin Dose Response Upon Addition of Camptothecin | | | | | Hyperbolic Fit Parameters of Camptothecin Dose Response Upon Addition of Nutlin | | |
|---|---|---|---|---|---|---|---|---|---|
| $2^{nd}$ Drug | Conc (µM) | $E_{max}$ | $\frac{1}{D50} \times 100$ | Source Data | $2^{nd}$ Drug | Conc (µM) | $E_{max}$ | $\frac{1}{D50} \times 100$ | Source Data |
| CPT | 0 | 38.0 +/− 12* | 28.6 +/− 4.7* | FIG. 5b | NUT | 0 | 61.9 +/− 25 | 10.8 +/− 16 | FIG. 5f |
| | 1 | 34.7 +/− 5.9 | N/A | FIG. 5c | | 1 | 105 +/− 160 | 1.97 +/− 7.7 | FIG. 5g |
| | 10 | 50.9 +/− 0.15 | 50.0 +/− 1.3* | FIG. 5d | | 25 | 109 +/− 4.1 | 3.18 +/− 0.40 | FIG. 5h |
| | 50 | 81.7 +/− 3.1* | 55.6 +/− 180 | FIG. 5e | | 125 | 221 +/− 400 | 0.62 +/− 1.8 | FIG. 5i |

TABLE 5

$E_{max}$ and $D_{50}$ values generated from combinatorial microarrays of CA2 CCSCs.
CA2

| | | Hyperbolic Fit Parameters of Nutlin Dose Response Upon Addition of Camptothecin | | | | | Hyperbolic Fit Parameters of Camptothecin Dose Response Upon Addition of Nutlin | | |
|---|---|---|---|---|---|---|---|---|---|
| $2^{nd}$ Drug | Conc (µM) | $E_{max}$ | $\frac{1}{D50} \times 100$ | Source Data | $2^{nd}$ Drug | Conc (µM) | $E_{max}$ | $\frac{1}{D50} \times 100$ | Source Data |
| CPT | 0 | 73.3 +/− 9.3* | 171 +/− 49 | FIG. 6b | NUT | 0 | 46.6 +/− 0.57 | 133 +/− 5.3* | FIG. 6f |
| | 1 | 43.8 +/− 11 | 189 +/− 328 | FIG. 6c | | 1 | 52.3 +/− 49 | 1.60 +/− 7.9* | FIG. 6g |
| | 10 | 57.0 +/− 39 | 0.95 +/− 4.6# | FIG. 6d | | 25 | 43.9 +/− 1.9 | N/A | FIG. 6h |
| | 50 | 34.1 +/− 9.3* | 303 +/− 260 | FIG. 6e | | 125 | N/A | 0.00 +/− 1.01# | FIG. 6i |

In CA1 cells, the $E_{max}$ of the nutlin-3a concentration response curve was increased by 115% when 50 µM camptothecin was present as compared to nutlin-3a alone (81.7 vs 38.0) (Table 4, FIGS. 14B, 14E). The sensitivity also increased by 75% when 10 µM camptothecin was present compared to nutlin-3a alone (50.0 vs 28.6) (Table 4, FIGS. 14B, 14D). By contrast, in CA2 cells the $E_{max}$ of the concentration response curve to nutlin-3a decreased by 53% when 50 µM camptothecin was present as compared to nutlin-3a alone, but not significantly (p=0.097) (FIGS. 14K and 14N). No statistical differences were found on the effects to sensitivity between the drugs in CA2 cells. The sensitivity of the CCSCs to nutlin-3a was unexpected due to the p53 mutation identified in these cells. However, responsiveness could potentially be explained by a nutlin-3a- erable variability in responses to drugs by CCSCs from different patients, and (ii) suggest that chemosensitivity screening on patient-derived CCSCs can lead to valuable information regarding chemotherapy decisions. Although efficacy of drugs against CCSCs was demonstrated, the approach could be adopted for any CSC or rare cellular subpopulation where cell numbers are limiting, and identifying responsiveness to drug combinations is paramount. This platform can facilitate personalized medicine approaches centered on the eradication of CCSCs.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

REFERENCES

1. Lee, M. J. et al. Sequential application of anticancer drugs enhances cell death by rewiring apoptotic signaling networks. *Cell* 149, 780-794 (2012).
2. Lake, R. A. & Robinson, B. W. Immunotherapy and chemotherapy—a practical partnership. *Nat Rev Cancer* 5, 397-405 (2005).
3. DeVita, V. T., Young, R. C. & Canellos, G. P. Combination versus single agent chemotherapy: a review of the basis for selection of drug treatment of cancer. *Cancer* 35, 98-110 (1975).
4. DeVita, V. T. & Chu, E. A history of cancer chemotherapy. *Cancer Res* 68, 8643-8653 (2008).
5. Lage, H. An overview of cancer multidrug resistance: a still unsolved problem. *Cell Mol Life Sci* 65, 3145-3167 (2008).
6. Maitland, M. L., DiRienzo, A. & Ratain, M. J. Interpreting disparate responses to cancer therapy: the role of human population genetics. *J Clin Oncol* 24, 2151-2157 (2006).
7. Magee, J. A., Piskounova, E. & Morrison, S. J. Cancer stem cells: impact, heterogeneity, and uncertainty. *Cancer Cell* 21, 283-296 (2012).
8. Shoemaker, R. H. et al. Development of human tumor cell line panels for use in disease-oriented drug screening. *Prog Clin Biol Res* 276, 265-286 (1988).
9. Ugurel, S. et al. In vitro drug sensitivity predicts response and survival after individualized sensitivity-directed chemotherapy in metastatic melanoma: a multicenter phase II trial of the Dermatologic Cooperative Oncology Group. *Clin Cancer Res* 12, 5454-5463 (2006).
10. Shackleton, M., Quintana, E., Fearon, E. R. & Morrison, S. J. Heterogeneity in cancer: cancer stem cells versus clonal evolution. *Cell* 138, 822-829 (2009).
11. Reya, T., Morrison, S. J., Clarke, M. F. & Weissman, I. L. Stem cells, cancer, and cancer stem cells. *Nature* 414, 105-111 (2001).
12. O'Brien, C. A., Kreso, A. & Jamieson, C. H. Cancer stem cells and self-renewal. *Clin Cancer Res* 16, 3113-3120 (2010).
13. Ricci-Vitiani, L. et al. Identification and expansion of human colon-cancer-initiating cells. *Nature* 445, 111-115 (2007).
14. Shenoy, A., Butterworth, E. & Huang, E. H. ALDH as a marker for enriching tumorigenic human colonic stem cells. *Methods Mol Biol* 916, 373-385 (2012).
15. Huang, E. H. et al. Aldehyde dehydrogenase 1 is a marker for normal and malignant human colonic stem cells (SC) and tracks SC overpopulation during colon tumorigenesis. *Cancer Res* 69, 3382-3389 (2009).
16. Boman, B. M. & Huang, E. Human colon cancer stem cells: a new paradigm in gastrointestinal oncology. *J Clin Oncol* 26, 2828-2838 (2008).
17. Shenoy, A. K. et al. Transition from colitis to cancer: high wnt activity sustains the tumor-initiating potential of colon cancer stem cell precursors. *Cancer Res* 72, 5091-5100 (2012).
18. Huang, E. H. & Wicha, M. S. Colon cancer stem cells: implications for prevention and therapy. *Trends Mol Med* 14, 503-509 (2008).
19. Zhao, C. et al. Hedgehog signalling is essential for maintenance of cancer stem cells in myeloid leukaemia. *Nature* 458, 776-779 (2009).
20. Acharya, A. P., Clare-Salzler, M. J. & Keselowsky, B. G. A high-throughput microparticle microarray platform for dendritic cell-targeting vaccines. *Biomaterials* 30, 4168-4177 (2009).
21. Hoe, K. K., Verma, C. S. & Lane, D. P. Drugging the p53 pathway: understanding the route to clinical efficacy. *Nat Rev Drug Discov* 13, 217-236 (2014).
22. Vassilev, L. T. et al. In vivo activation of the p53 pathway by small-molecule antagonists of MDM2. *Science* 303, 844-848 (2004).
23. Vassilev, L. T. p53 Activation by small molecules: application in oncology. *J Med Chem* 48, 4491-4499 (2005).
24. Goldwasser, F., Bae, I., Valenti, M., Torres, K. & Pommier, Y. Topoisomerase I-related parameters and camptothecin activity in the colon carcinoma cell lines from the National Cancer Institute anticancer screen. *Cancer Res* 55, 2116-2121 (1995).
25. Motwani, M. et al. Augmentation of apoptosis and tumor regression by flavopiridol in the presence of CPT-11 in Hct116 colon cancer monolayers and xenografts. *Clin Cancer Res* 7, 4209-4219 (2001).
26. Soen, Y., Mori, A., Palmer, T. D. & Brown, P. O. Exploring the regulation of human neural precursor cell differentiation using arrays of signaling microenvironments. *Mol Syst Biol* 2, 37 (2006).
27. Bailey, S. N., Sabatini, D. M. & Stockwell, B. R. Microarrays of small molecules embedded in biodegradable polymers for use in mammalian cell-based screens. *Proc Natl Acad Sci USA* 101, 16144-16149 (2004).
28. Lau, L. M., Nugent, J. K., Zhao, X. & Irwin, M. S. HDM2 antagonist Nutlin-3 disrupts p73-HDM2 binding and enhances p73 function. *Oncogene* 27, 997-1003 (2008).
29. Langer, R. et al. Controlled release and magnetically modulated systems for macromolecular drugs. *Ann N Y Acad Sci* 446, 1-13 (1985).
30. Langer, R., Brem, H. & Tapper, D. Biocompatibility of polymeric delivery systems for macromolecules. *J Biomed Mater Res* 15, 267-277 (1981).
31. Sefton, M. V., Brown, L. R. & Langer, R. S. Ethylene-vinyl acetate copolymer microspheres for controlled release of macromolecules. *J Pharm Sci* 73, 1859-1861 (1984).

32. Carpentino, J. E. et al. Aldehyde dehydrogenase-expressing colon stem cells contribute to tumorigenesis in the transition from colitis to cancer. *Cancer Res* 69, 8208-8215 (2009).
33. Sanchez, J. A., Dejulius, K. L., Bronner, M., Church, J. M. & Kalady, M. F. Relative role of methylator and tumor suppressor pathways in ulcerative colitis-associated colon cancer. *Inflamm Bowel Dis* 17, 1966-1970 (2011).
34. Tallarida, R. (2000).
35. Gupta, M. et al. Inactivation of p53 increases the cytotoxicity of camptothecin in human colon HCT116 and breast MCF-7 cancer cells. *Clin Cancer Res* 3, 1653-1660 (1997).
36. Kranz, D. & Dobbelstein, M. Nongenotoxic p53 activation protects cells against S-phase-specific chemotherapy. *Cancer Res* 66, 10274-10280 (2006).

Therefore the following is claimed:

1. An array, comprising:
   a substrate having a first area of the array and a plurality of cell binding areas distinct from the first area;
   a first bonding layer disposed on the substrate in the first area of the array;
   a second bonding layer disposed on the first bonding layer;
   a non-fouling layer disposed on the second bonding layer in a first area of the array, wherein cells do not substantially adhere to the non-fouling layer; and
   a plurality of cell binding sites corresponding to the cell binding areas, each cell binding site comprising:
   an adhesive layer disposed on the substrate in each cell binding site area of the array distinct from the non-fouling layer;
   a timed-release polymer layer disposed on the adhesive layer in each cell binding site, each timed-release polymer layer comprising one or more thin films, each thin film including one or more types of a time release agent, wherein the timed-release polymer layer of at least one cell binding site comprises at least one type of agent different from at least one type of agent in the timed-release polymer layer of at least one other cell binding site or comprises a different concentration of agent than the concentration of agent in the timed-release polymer layer of at least one other cell binding site, and
   a cell adhesion layer disposed on the timed-release polymer layer in each cell binding site, wherein one or more types of target cells adhere to the cell adhesion layer, the timed-release polymer layer having the characteristic of releasing the agent to the cell or cells adhered to the cell binding site.

2. The array of claim 1, wherein one of type target cell, a first target cell, has an affinity for another type of target cell, a second target cell, wherein both the first target cell and the second target cell are disposed on the cell binding site, the timed-release polymer having the characteristic of releasing the agent to the first target cell and the second target cell adhered to the cell binding site.

3. The array of claim 1, wherein the cell binding sites have an area of about 20 $\mu m^2$ to 5 $mm^2$ and wherein a pair of cell binding sites is positioned about 10 $\mu m$ to 2 mm from one another.

4. The array of claim 1, wherein the timed-release polymer layer of at least one cell binding site comprises at least one type of agent different from at least one type of agent in the timed-release polymer layer of at least one other cell binding site.

5. The array of claim 1, wherein the timed-release polymer layer of at least one cell binding site comprises a first concentration of one type of agent different from a concentration of that type of agent in the timed-release polymer layer of at least one other cell binding site.

6. The array of claim 1, wherein multiple cell binding sites have one or more different types of agent in the timed-release polymer layer than the types of agent in the timed-release polymer layers of other cell binding sites.

7. The array of claim 1, wherein multiple cell binding sites have one or more different types of agents or combinations of agents present in different concentrations than the types and combinations of agents in the timed-release polymer layers of other cell binding sites.

8. The array of claim 1, wherein the array comprises at least a first and second type of agent, wherein the first agent is present in at least two different concentrations in the timed-release polymer layers of at least two different cell binding sites and the second agent is present in at least two different concentrations in at least two different cell binding sites, and wherein the first agent and second agent are combined in different concentrations in at least two different cell binding sites.

9. The array of claim 1, wherein at least one agent comprises nutlin-3a.

10. The array of claim 1, wherein at least one agent comprises camptothecin.

11. The array of claim 1, wherein at least one type of target cell is a cancer stem cell.

12. The array of claim 11, wherein the cancer stem cell is a colorectal cancer stem-like cell.

13. The array of claim 1, wherein the timed-release polymer layer is selected from the group consisting of: a poly(lactic-co-glycolic acid), polycaprolactone, polyglycolide, polylactic acid, poly(vinylpyridine), chitosan, alginate, and a combination thereof.

14. The array of claim 1, wherein the timed-release polymer layer includes a plurality of layers each having a thickness of about 10 nm to 5 $\mu m$.

15. The array of claim 1, wherein the cell adhesion layer is selected from the group consisting of: fibronectin, polylysine, collagen, vitronectin, intercellular adhesion molecules, immunoglobulin superfamily Cell Adhesion Molecules (IgSF CAMs), Neural Cell Adhesion Molecules (NCAMs), Intercellular Cell Adhesion Molecules (ICAM-1), Vascular Cell Adhesion Molecules (VCAM-1), Platelet-endothelial Cell Adhesion Molecules (PECAM-1), L1 Cell Adhesion Molecules (L1), integrin, cadherin, and a combination thereof.

16. An array, comprising:
   a substrate having a first area and a plurality of cell binding site areas distinct from the first area, wherein the first area of the array comprises:
   a first bonding layer disposed on the first area of the first substrate;
   a second bonding layer disposed on the first bonding layer;
   a non-fouling layer disposed on the second bonding layer, wherein cells do not adhere to the non-fouling layer; and
   wherein the cell binding site areas comprise:
   an adhesive layer disposed on each of the cell binding site areas of the first substrate;
   a timed-release polymer layer disposed on the adhesive layer, wherein the timed-release polymer layer comprises one or more thin films including one or more agents, wherein the timed-release polymer layer of at least one cell binding site comprises a different concentration of agent than the concentration of agent in the timed-release polymer layer of at least one other cell binding site; and a cell adhesion layer disposed on the timed-release polymer layer.

17. The array of claim 16, wherein the first bonding layer is selected from the group consisting of: titanium, nickel, chromium, and a combination thereof.

18. The array of claim 16, wherein the second bonding layer is selected from the group consisting of: gold, silver, copper, palladium, platinum, nickel, alloys of each of these, and a combination thereof.

19. The array of claim 16, wherein the adhesive layer is selected from the group consisting of: a silane, a compound including an ethylene oxide group, a compound including a acrylamide group, a compound including an amine group, a compound including a hydrophobic group, and a combination thereof.

* * * * *